United States Patent [19]

Leppard et al.

[11] Patent Number: 5,767,169

[45] Date of Patent: Jun. 16, 1998

[54] PHOTOPOLYMERIZABLE COMPOSITIONS COMPRISING ALKOXYPHENYL-SUBSTITUTED BISACYLPHOSPHINE OXIDES

[75] Inventors: David George Leppard, Marly, Switzerland; Manfred Köhler, Freiburg, Germany

[73] Assignee: Ciba Specialty Chemicals Corporation, Tarrytown, N.Y.

[21] Appl. No.: 601,595

[22] Filed: Feb. 14, 1996

Related U.S. Application Data

[62] Division of Ser. No. 519,225, Aug. 25, 1995.

[30] Foreign Application Priority Data

Sep. 2, 1994 [CH] Switzerland ............... 2691/94

[51] Int. Cl.⁶ ............................................. C08F 2/46
[52] U.S. Cl. ..................... 522/64; 522/18; 430/281.1; 430/916; 430/923
[58] Field of Search ............... 522/18, 64; 430/281.1, 430/916, 923

[56] References Cited

U.S. PATENT DOCUMENTS

| | | | |
|---|---|---|---|
| 4,737,593 | 4/1988 | Ellrich et al. | 568/15 |
| 4,792,632 | 12/1988 | Ellrich et al. | 568/15 |
| 4,868,091 | 9/1989 | Boettcher et al. | 430/281.1 |
| 5,100,929 | 3/1992 | Jochum et al. | 522/64 |

FOREIGN PATENT DOCUMENTS

| | | | |
|---|---|---|---|
| 2525192 | 4/1993 | Australia | C07F 9/53 |
| 0184095 | 6/1986 | European Pat. Off. | C08F 2/50 |
| 0262629 | 4/1988 | European Pat. Off. | |
| 0446175 | 9/1991 | European Pat. Off. | |
| 4231579 | 3/1993 | Germany | C07F 9/53 |
| 2259704 | 3/1993 | United Kingdom | C07F 9/53 |

OTHER PUBLICATIONS

Derwent Abstract 91-269010/37 of EP-A-446175.

*Primary Examiner*—George F. Lesmes
*Assistant Examiner*—Bernard P. Codd
*Attorney, Agent, or Firm*—Michele A. Kovaleski; Victoria M. Malia

[57] ABSTRACT

A photopolymerizable composition comprising (a) at least one ethylenically unsaturated photopolymerizable compound, and (b) alkoxyphenyl-substituted bisacylphosphine oxides of the formula I

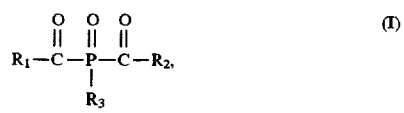

in which $R_1$ and $R_2$ are identical or different and are a radical of the formula II

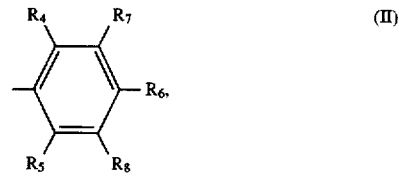

in which $R_4$ and $R_5$ independently of one another are $C_1$–$C_{12}$ alkyl or $C_1$–$C_{12}$ alkoxy, and $R_6$, $R_7$ and $R_8$ independently of one another are hydrogen, $C_1$–$C_{12}$ alkyl, $C_1$–$C_{12}$ alkoxy or halogen, $R_3$ is a radical of the formula III

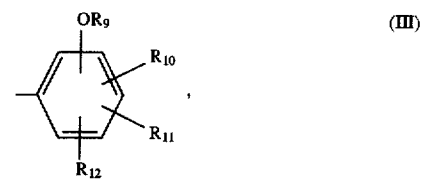

in which $R_9$ is $C_1$–$C_{20}$ alkyl, $C_2$–$C_{20}$ alkyl, $C_5$–$C_6$ cycloalkyl, phenyl, naphthyl, phenyl-$C_1$–$C_5$ alkyl, $C_2$–$C_{12}$ alkenyl, —$CF_3$ or

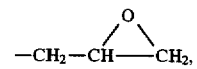

or $R_9$ is a radical of the formula IV or V

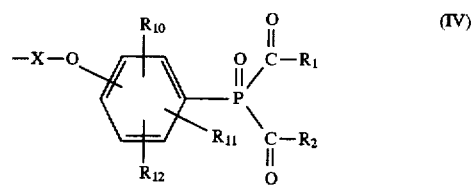

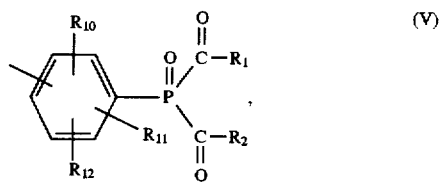

in which X is for example $C_1$–$C_{16}$ alkylene, $C_4$–$C_{12}$ alkenylene or is xylylene, $R_{10}$ is for example hydrogen, $C_1$–$C_{20}$ alkyl, $C_2$–$C_{12}$ alkenyl, cyclopentyl, cyclohexyl, phenyl with 1 or 2 $C_1$–$C_4$ alkyl and/or $C_1$–$C_4$ alkoxy groups, or is $C_1$–$C_4$ alkoxy.

$R_{11}$ is hydrogen, $C_1$–$C_{20}$ alkyl, $C_2$–$C_{12}$ alkenyl, cyclopentyl, cyclohexyl, phenyl, or is $C_1$–$C_4$ alkoxy, or is a radical of the formula VI

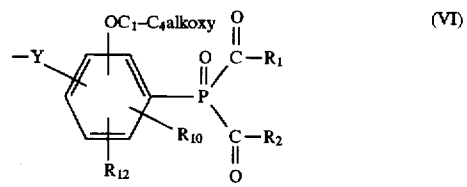

or $R_9$ and $R_{11}$, in the formula III together are ethylene, —$CH_2CR_{14}R_{15}$— or —$C(CH_3)_2CH=CH$—,
or
$R_{10}$ and $R_{11}$, together with the atoms to which they are attached, for example form a benzene ring,
$R_{12}$ is hydrogen or $C_1$–$C_4$ alkoxy,
$R_{13}$ is $C_1$–$C_4$ alkyl,
$R_{14}$ and $R_{15}$ independently of one another are hydrogen, $C_1$–$C_8$ alkyl, phenyl or —$CH_2OR_{13}$, or $R_{14}$ and $R_{15}$, together with the carbon atom to which they attached, form a $C_5$–$C_6$ cycloalkyl ring,
Y is for example a single bond, —$CR_{16}R_{17}$— or —$CH=CH$—, $R_{16}$ is hydrogen, methyl or ethyl,
$R_{17}$ is hydrogen or $C_1$–$C_4$ alkyl,
$R_{18}$ is hydrogen, $C_1$–$C_{12}$ alkyl or phenyl, and m is a number from 2–12, with the proviso that if the radical —$OR_9$ in the formula III is in the p-position of the phenyl ring and $R_9$ is methyl, at least one of the radicals $R_{10}$, $R_{11}$ and $R_{12}$ is not hydrogen, are suitable for the photopolymerization of compounds containing ethylenically unsaturated bonds.

5 Claims, No Drawings

PHOTOPOLYMERIZABLE COMPOSITIONS COMPRISING ALKOXYPHENYL-SUBSTITUTED BISACYLPHOSPHINE OXIDES

This is a divisional of Ser. No. 08/519,225, filed Aug. 25, 1995 pending.

The invention relates to alkoxyphenyl-substituted bisacylphosphine oxide compounds, to compositions comprising these compounds and to the use of the compounds as photoinitiators for the photopolymerization of ethylenically unsaturated compounds.

Bisacylphosphine oxide compounds are known as photoinitiators. Such compounds are described, for example, in GB-A 2 259 704 and in U.S. Pat. No. 4 792 632 and U.S. Pat. No. 4 868 091. The compounds disclosed therein include, inter alia, bis(2,6-dichlorobenzoyl)4-ethoxyphenylphosphine oxide and bis(2,6-dichlorobenzoyl)-2,4-dimethoxyphenylphosphine oxide. EP-A 446 175 discloses photoinitiator mixtures comprising mono- and bisacylphosphine oxides with α-hydroxy ketones and benzophenones. Inter alia, bis(2,4,6-trimethylbenzoyl)-4-methoxyphenylphosphine oxide is disclosed as a possible acylphosphine oxide component in such a mixture.

In industry, for the extensive range of applications of photoinitiators, there continues to be a need for reactive storage- and hydrolysis-stable photoinitiators having good surface curing properties.

It has now been found that these properties are present in the compounds of the formula I

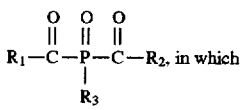

$R_1$ and $R_2$ are identical or different and are a radical of the formula II

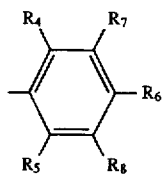

in which $R_4$ and $R_5$ independently of one another are $C_1$–$C_{12}$alkyl or $C_1$–$C_{12}$alkoxy, and $R_6$, $R_7$ and $R_8$ independently of one another are hydrogen, $C_1$–$C_{12}$alkyl, $C_1$–$C_{12}$alkoxy or halogen, $R_3$ is a radical of the formula III

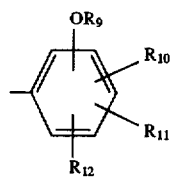

in which $R_9$ is $C_1$–$C_{20}$alkyl, $C_2$–$C_{20}$ alkyl which is interrupted by O, $C_2$–$C_{12}$ alkenoxy-substituted $C_1$–$C_4$alkyl, halogen-substituted $C_1$–$C_{20}$alkyl, $C_5$–$C_6$cycloalkyl, phenyl which is unsubstituted or is substituted with 1–4 $C_1$–$C_4$alkyl and/or $C_1$–$C_4$alkoxy groups, naphthyl which is unsubstituted or is substituted with 1–4 $C_1$–$C_4$alkyl and/or $C_1$–$C_4$alkoxy groups, phenyl-$C_1$–$C_5$alkyl which is unsubstituted or is substituted on the phenyl ring with 1–4 $C_1$–$C_4$alkyl and/or $C_1$–$C_4$alkoxy groups, or is $C_2$–$C_{12}$alkenyl, —$CF_3$ or

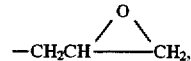

or $R_9$ is a radical of the formula IV or V

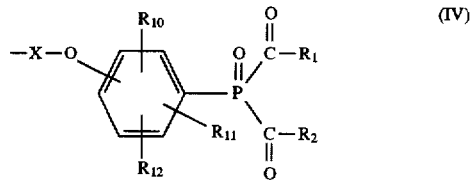

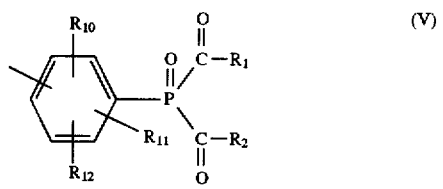

in which $R_1$ and $R_2$ are as defined above.

X is unsubstituted or —$OR_{13}$-substituted $C_1$–$C_{16}$alkylene, $C_2$–$C_{20}$alkylene which is interrupted by O, or is $C_4$–$C_{12}$alkenylene or xylylene.

$R_{10}$ is hydrogen, $C_1$–$C_{20}$alkyl, $C_2$–$C_{18}$alkyl which is interrupted by O, or is $C_2$–$C_{12}$alkenyl, cyclopentyl, cyclohexyl, phenyl which is unsubstituted or is substituted with 1 or 2 $C_1$–$C_4$alkyl and/or $C_1$–$C_4$alkoxy groups, or is $C_1$–$C_4$alkoxy.

$R_{11}$ is hydrogen, $C_1$–$C_{20}$alkyl, $C_2$–$C_{18}$alkyl which is interrupted by O, or is $C_2$–$C_{12}$alkenyl, cyclopentyl, cyclohexyl, phenyl which is unsubstituted or is substituted with 1 or 2 $C_1$–$C_4$alkyl and/or $C_1$–$C_4$alkoxy groups, or is $C_1$–$C_4$ alkoxy, or is a radical of the formula VI

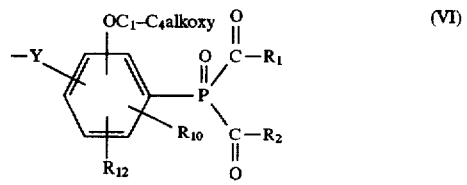

or $R_9$ and $R_{11}$ in the formula III together are —$CH_2CR_{14}R_{15}$— or —$C(CH_3)_2CH$=$CH$—, or $R_{10}$ and $R_{11}$, together with the atoms to which they are attached, form a benzene ring which is unsubstituted or substituted with 1 or 2 $C_1$–$C_4$alkyl and/or $C_1$–$C_4$alkoxy groups, $R_{12}$ is hydrogen or $C_1$–$C_4$alkoxy, $R_{13}$ is $C_1$–$C_8$alkyl, $R_{14}$ and $R_{15}$ independently of one another are hydrogen, $C_1$–$C_8$alkyl, phenyl or —$CH_2OR_{13}$, or $R_{14}$ and $R_{15}$, together with the carbon atom to which they attached, form a $C_5$–$C_6$cycloalkyl ring, Y is a single bond, —$CR_{16}R_{17}$—, —$NR_{18}$—, —S—, —$SO_2$—, —$(CH_2)_m$— or —$CH$=$CH$—, $R_{16}$ is hydrogen, methyl or ethyl, $R_{17}$ is hydrogen or $C_1$–$C_4$allyl, $R_{18}$ is hydrogen, $C_1$–$C_{12}$alkyl or phenyl, and m is a number from 2–12, with the proviso that if the radical —$OR_9$ in the formula III is in the p-position of the phenyl ring and $R_9$ is methyl, at least one of the radicals $R_{10}$, $R_{11}$ and $R_{12}$ is not hydrogen.

$R_4$, $R_5$, $R_6$, $R_7$ and $R_8$ as $C_1$–$C_{12}$alkyl are linear or branched radicals and are for example methyl, ethyl, propyl, isopropyl, n-butyl, sec-butyl, isobutyl, tert-butyl, pentyl, hexyl, heptyl, 2,4,4-trimethylpentyl, 2-ethylhexyl, octyl, nonyl, decyl or dodecyl. Examples are $R_4$, $R_5$, $R_6$, $R_7$ and $R_8$ as $C_1$–$C_8$alkyl, especially $C_1$–$C_4$alkyl.

$R_4$, $R_5$, $R_6$, $R_7$, $R_8$ as $C_1$–$C_{12}$alkoxy are linear or branched radicals and are for example methoxy, ethoxy, propoxy, isopropoxy, n-butyloxy, sec-butyloxy, isobutyloxy, tert-butyloxy, pentyloxy, hexyloxy, heptyloxy, 2,4,4-trimethylpentyloxy, 2-ethylhexyloxy, octyloxy, nonyloxy, decyloxy or dodecyloxy, especially methoxy, ethoxy, propoxy, isopropoxy, n-butyloxy, sec-butyloxy, isobutyloxy, tert-butyloxy, preferably methoxy.

Halogen is fluorine, chlorine, bromine and iodine, especially chlorine and bromine, preferably chlorine.

Examples of $C_1$–$C_4$alkoxy substituents are methoxy, ethoxy, propoxy or butoxy, especially methoxy.

$R_9$, $R_{10}$ and $R_{11}$ as $C_1$–$C_{20}$alkyl are linear or branched and are for example methyl, ethyl, propyl, isopropyl, n-butyl, sec-butyl, isobutyl, tert-butyl, pentyl, hexyl, heptyl, 2,4,4-trimethylpentyl, 2-ethylhexyl, octyl, nonyl, decyl, dodecyl, tetradecyl, heptadecyl, octadecyl, nonadecyl or eicosyl. $R_9$ for example is $C_1$–$C_{18}$alkyl, especially $C_1$–$C_{12}$alkyl, preferably $C_3$–$C_{12}$alkyl, for example $C_4$–$C_{12}$alkyl. $R_9$ is preferably methyl or isopropyl.

Where $C_1$–$C_{20}$alkyl is substituted with one or more halogens, then there are for example 1–3 or 1 or 2 halogen substituents on the alkyl radical.

$R_9$ as $C_2$–$C_{20}$alkyl which is interrupted one or more times by O is for example interrupted 1–9, e.g. 1–7 or 1 or 2 times, by O. Examples of such radicals are linear or branched $C_1$–$C_8$alkoxy, for example methoxy, ethoxy, propoxy, isopropoxy, n-butyloxy, sec-butyloxy, isobutyloxy, tert-butyloxy, pentyloxy, hexyloxy, heptyloxy, 2,4,4-trimethylpentyloxy, 2-ethylhexyloxy, octyloxy, or —CH$_2$CH$_2$—O—CH$_3$, —CH$_2$CH$_2$—O—CH$_2$CH$_3$, —[CH$_2$CH$_2$O]$_y$—CH$_3$, where y=1–9, —(CH$_2$CH$_2$O)$_7$CH$_2$CH$_3$ or —CH$_2$—CH(CH$_3$)—O—CH$_2$—CH$_2$CH$_3$.

$C_2$–$C_{12}$Alkenoxy substituents on $R_9$ as $C_1$–$C_4$alkyl are for example ethenyloxy, 2-propenyloxy, 2-methyl-2-propenyloxy, 1,1-dimethyl-2-propenyloxy, 1-butenyloxy, 2-butenyloxy, 3-butenyloxy, 5-hexenyloxy, 7-octenyloxy, 9-decenyloxy or 11-dodecenyloxy, especially 2-propenyloxy.

$R_9$ as $C_5$–$C_6$cycloalkyl is cyclopentyl or cyclohexyl, especially cyclohexyl.

$R_9$ as substituted phenyl or naphthyl is substituted from one to four times, for example one, two or three times, especially two or three times.

$R_9$ as substituted phenyl or naphthyl is substituted for example with linear or branched $C_1$–$C_4$alkyl such as methyl, ethyl, n-propyl, isopropyl, n-butyl, isobutyl, s-butyl or t-butyl, or with linear or branched $C_1$–$C_4$alkoxy such as methoxy, ethoxy, n-propoxy, isopropoxy, n-butoxy, isobutoxy, s-butoxy or t-butoxy. Preferred substituents for $R_9$ as phenyl or naphthyl are, in particular, methyl and methoxy.

$R_9$ as phenyl-$C_1$–$C_5$alkyl is for example benzyl, phenylethyl, α-methylbenzyl, phenylpentyl or α,α-dimethylbenzyl, especially benzyl. Substituted phenyl-$C_1$–$C_5$alkyl is substituted from one to four times, for example one, two or three times, especially two or three times, on the phenyl ring. Appropriate $C_1$–$C_4$alkyl or $C_1$–$C_4$alkoxy substituents are linear or branched and examples are methyl, ethyl, propyl, n-butyl, t-butyl, especially methyl, methoxy, ethoxy, propoxy or butoxy, especially methoxy. $R_9$, $R_{10}$ and $R_{11}$ as $C_2$–$C_{12}$alkenyl may be mono- or polyunsaturated and are for example allyl, methallyl, 1,1-dimethylallyl, 1-butenyl, 3-butenyl, 2-butenyl, 1,3-pentadienyl, 5-hexenyl, 7-octenyl or 8-nonenyl, especially allyl.

X as $C_1$–$C_{16}$alkylene is linear or branched alkylene such as, for example, methylene, ethylene, propylene, 1-methylethylene, 1,1-dimethylethylene, butylene, 1-methylpropylene, 2-methylpropylene, pentylene, hexylene, heptylene, octylene, nonylene, decylene, dodecylene, tetradecylene or hexadecylene. X is in particular $C_1$–$C_{12}$alkylene, for example ethylene, decylene,

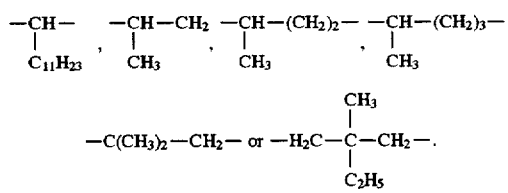

O$R_{13}$-substituted $C_1$–$C_{16}$alkylene is for example

—CH—
|
OCH$_3$

Where X is $C_2$–$C_{20}$alkylene interrupted by —O—, examples of the resulting structural units are —CH$_2$—O—CH$_2$—, —CH$_2$CH$_2$—O—CH$_2$CH$_2$—, —[CH$_2$CH$_2$O]$_y$—, where y=1–9, —(CH$_2$CH$_2$O)$_7$CH$_2$CH$_2$— or —CH$_2$—CH(CH$_3$)—O—CH$_2$—CH(CH$_3$)—.

X as $C_4$–$C_{12}$alkenylene may be mono- or polyunsaturated and is for example 1-butenylene, 3-butenylene, 2-butenylene, 1,3-pentadienylene, 5-hexenylene, 7-octenylene, 10-decenylene or 12-dodecenylene.

Where $R_{10}$ or $R_{11}$ are $C_2$–$C_{18}$alkyl interrupted by O, examples of the resulting structural units are —CH$_2$CH$_2$—O——CH$_3$, —CH$_2$CH$_2$—O—CH$_2$CH$_3$, —[CH$_2$CH$_2$O]$_y$CH$_3$, where y=1–8, —(CH$_2$CH$_2$O)$_7$CH$_2$CH$_3$ or —CH$_2$—CH(CH$_3$)—O—CH$_2$—CH$_2$CH$_3$.

In radicals $R_{10}$ and $R_{11}$ as phenyl substituted with 1 or 2 $C_1$–$C_4$alkyl and/or $C_1$–$C_4$alkoxy groups, the substituents are preferably in the 2-, 4- or 2,4-position of the phenyl ring. The substituents are linear or branched and are for example methyl, ethyl, n-propyl, isopropyl, n-butyl, isobutyl, s-butyl, t-butyl, methoxy, ethoxy, n-propoxy, isopropoxy, n-butoxy, isobutoxy, s-butoxy, t-butoxy. Preferred substituents are methyl and methoxy.

Where $R_9$ and $R_{11}$ in the formula III are ethylene, —CH$_2$CR$_{14}$R$_{15}$— or —C(CH$_3$)$_2$CH=CH—, examples of the resulting structural units are

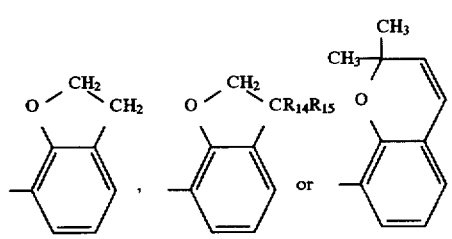

Where $R_{10}$ and $R_{11}$, together with the atoms to which they are attached, form a benzene ring, examples of the resulting structural units are

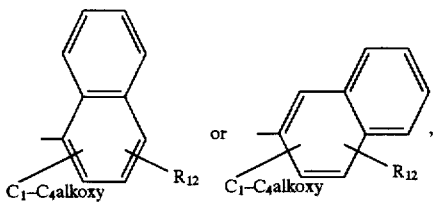

the fused benzene ring being unsubstituted or substituted with one or two $C_1$–$C_4$alkyl and/or $C_1$–$C_4$alkoxy radicals. The substituents are linear or branched and are for example methyl, ethyl, n-propyl, isopropyl, n-butyl, isobutyl, s-butyl, t-butyl, methoxy, ethoxy, n-propoxy, isopropoxy, n-butoxy, isobutoxy, s-butoxy, t-butoxy. Preferred substituents are methyl and methoxy.

$R_{13}$ as $C_1$–$C_8$alkyl is linear or branched and is for example methyl, ethyl, n-propyl, isopropyl, n-butyl, iso-butyl, s-butyl, t-butyl, pentyl, hexyl, heptyl or octyl. $R_{13}$ is in particular $C_1$–$C_4$alkyl.

$R_{14}$ and $R_{15}$ as $C_1$–$C_8$alkyl are linear or branched radicals and are for example methyl, ethyl, propyl, isopropyl, n-butyl, sec-butyl, isobutyl, tert-butyl, pentyl, hexyl, heptyl, 2,4,4-trimethylpentyl, 2-ethylhexyl or octyl. For example, $R_{14}$ and $R_{15}$ is $C_1$–$C_6$alkyl, especially $C_1$–$C_4$alkyl.

Where $R_{18}$ is $C_1$–$C_{12}$alkyl, the radicals are linear or branched and are for example methyl, ethyl, propyl, isopropyl, n-butyl, sec-butyl, isobutyl, tert-butyl, pentyl, hexyl, heptyl, 2,4,4-trimethylpentyl, 2-ethylhexyl, octyl, nonyl, decyl or dodecyl. For example, $R_{18}$ is $C_1$–$C_8$alkyl, especially $C_1$–$C_4$alkyl.

Where $R_{14}$ and $R_{15}$, together with the carbon atom to which they are attached, form a $C_5$–$C_6$cycloalkyl ring, then this is a cyclohexyl or cyclopentyl ring.

Examples of compounds according to the invention are:
bis(2,4,6-trimethylbenzoyl)-2,4-diisobutoxyphenylphosphine oxide,
bis(2,4,6-trimethylbenzoyl)-2,4-dioctyloxyphenylphosphine oxide,
bis(2,4,6-trimethylbenzoyl)-2,4-diisopropoxyphenylphosphine oxide,
bis(2,4,6-trimethylbenzoyl)-2,4-dihexyloxyphenylphosphine oxide,
bis(2,4,6-trimethylbenzoyl)-2,4-di-sec-butoxyphenylphosphine oxide,
bis(2,4,6-trimethylbenzoyl)-2-methyl-4-methoxyphenylphosphine oxide,
bis(2,4,6-trimethylbenzoyl)-2-propoxy-4-methylphenylphosphine oxide,
bis(2,4,6-trimethylbenzoyl)-2,4-diisopentyloxyphenylphosphine oxide,
bis(2,4,6trimethylbenzoyl)-2,6-dimethyl-4-butoxyphenylphosphine oxide,
bis(2,6-dimethoxybenzoyl)-2,4-dioctyloxyphenylphosphine oxide,
bis(2,6-dimethoxybenzoyl)-2,4-diisobutoxyphenylphosphine oxide,
bis(2,6-dimethoxybenzoyl)-2-methyl-4-methoxyphenylphosphine oxide or
bis(2,6-direthoxybenzoyl)-2-propoxy-4-methylphenylphosphine oxide.

Preferred compounds of the formula I are those which in formula III at least one ortho position of the phenyl ring is not occupied by hydrogen.

Further interesting compounds of the formula I are those in which $R_9$ is $C_1$–$C_{12}$alkyl, $C_2$–$C_{12}$alkyl which is interrupted by O, $C_1$–$C_4$alkyl which is substituted with $C_3$–$C_8$alkenoxy, or is cyclopentyl, cyclohexyl, phenyl which is unsubstituted or substituted with 1–4 $C_1$–$C_4$alkyl and/or $C_1$–$C_4$alkoxy groups, benzyl which is unsubstituted or is substituted on the phenyl ring with 1–4 $C_1$–$C_4$alkyl and/or $C_1$–$C_4$alkoxy groups, or is $C_3$–$C_8$alkenyl, or $R_9$ is a radical of the formula IV or V, X is unsubstituted or —$OR_{13}$-substituted $C_1$–$C_{12}$alkylene, $C_3$–$C_{18}$alkylene which is interrupted by O, or is $C_4$–$C_8$alkenylene or xylylene, $R_{10}$ is hydrogen, $C_1$–$C_{12}$alkyl, $C_3$–$C_{18}$alkyl which is interrupted by O, or is $C_3$–$C_8$alkenyl, cyclopentyl, cyclohexyl, phenyl or $C_1$–$C_4$alkoxy, or $R_9$ and $R_{10}$ in the formula III are together —$CH_2CH_2$—.

$R_{11}$ is hydrogen, $C_1$–$C_{12}$alkyl, $C_3$–$C_{18}$alkyl which is interrupted by O, or is $C_3$–$C_8$alkenyl, cyclopentyl, cyclohexyl, phenyl or $C_1$–$C_4$alkoxy, or is a radical of the formula VIa

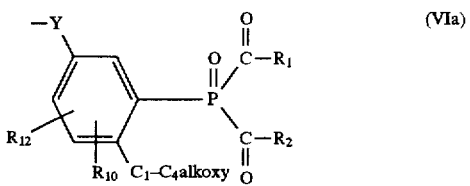

Y is a single bond, —$CR_{16}R_{17}$— or —S—,
$R_{13}$ is $C_1$–$C_4$alkyl, and
$R_{16}$ and $R_{17}$ are hydrogen or methyl.

Compounds of the formula I which are worthy of emphasis are those in which $R_3$ is a radical of the formula IIIa

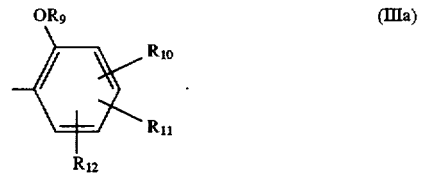

Particular preference is given to those compounds of the formula I in which $R_{10}$ in formula IIIa is $C_1$–$C_4$alkoxy.

Preference is also given to compounds of the formula I in which $R_{10}$ is in the ortho-position of the phenyl ring and is $C_1$–$C_4$alkoxy.

Also of interest are compounds of the formula I in which $R_3$ is a radical of the formula IIIe

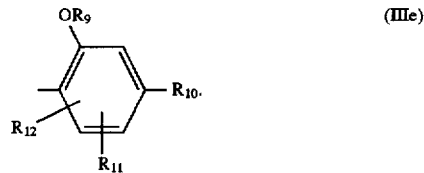

Compounds of the formula I which are of interest are those in which $R_3$ is a group of the formula IIIb

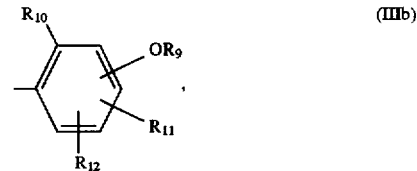

in which
$R_{10}$ is $C_1$–$C_{12}$alkyl, $C_3$–$C_{18}$alkyl which is interrupted by O, or is $C_3$–$C_8$alkenyl, cyclopentyl, cyclohexyl or phenyl, or
$R_9$ and $R_{10}$ in the formula IIIb are together —$CH_2CH_2$—, and $R_{11}$ is hydrogen, $C_1$–$C_{12}$alkyl, $C_3$–$C_{18}$alkyl which is interrupted by O, or is $C_3$–$C_8$alkenyl, cyclopentyl, cyclohexyl, phenyl or $C_1$–$C_4$alkoxy.

Preference is additionally given to the compounds of the formula I in which $R_3$ is a radical of the formula IIIc

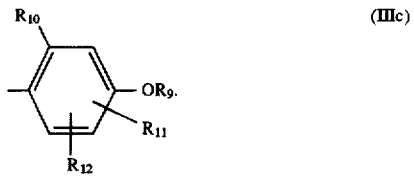

(IIIc)

Likewise preferred are compounds of the formula I in which $R_3$ is a radical of the formula IIId

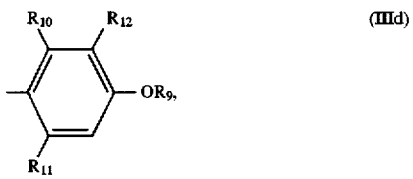

(IIId)

$R_9$ is $C_1$–$C_8$alkyl, $C_3$–$C_{12}$alkyl which is interrupted once by —O—, or is cyclohexyl, phenyl, benzyl, allyl or a radical of the formula IVb or Vb

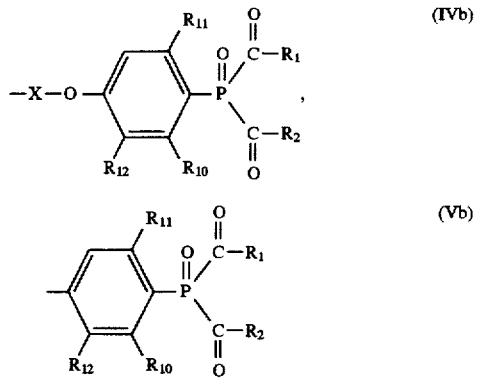

(IVb)

(Vb)

X is $C_1$–$C_8$alkylene, $C_4$–$C_8$alkylene which is interrupted by —O—, or is xylylene, $R_{11}$ is hydrogen, $C_1$–$C_{12}$alkyl, $C_3$–$C_{18}$alkyl which is interrupted by O, or is $C_3$–$C_8$alkenyl, cyclopentyl, cyclohexyl or phenyl, and $R_{12}$ is hydrogen or $C_1$–$C_4$alkoxy.

Further preferred compounds of the formula I are those in which $R_9$ is $C_1$–$C_8$alkyl, $C_3$–$C_8$alkyl which is interrupted by —O—, or is benzyl, allyl or a radical of the formula IVb or Vb, X is $C_1$–$C_4$alkylene, $R_{10}$ is $C_1$–$C_{12}$alkyl, $R_{11}$ is hydrogen or methyl and $R_{12}$ is hydrogen.

Also of interest are compounds of the formula I in which $R_9$ is $C_3$–$C_{12}$alkyl, especially $C_4$–$C_{12}$alkyl.

Preference is additionally given to compounds of the formula I in which $R_4$ and $R_5$ independently of one another are $C_1$–$C_{12}$alkyl or $C_1$–$C_{12}$alkoxy, $R_6$ is hydrogen, $C_1$–$C_{12}$alkyl or $C_1$–$C_{12}$alkoxy, $R_7$ is hydrogen or $C_1$–$C_4$alkyl and $R_8$ is hydrogen.

Other compounds of the formula I which are of interest are those in which $R_4$ and $R_5$ independently of one another are methyl or methoxy, $R_6$ is hydrogen or methyl, and $R_7$ and $R_8$ are hydrogen.

Of particular interest are compounds of the formula I in which $R_1$ and $R_2$ are identical.

Preference is given to compounds of the formula I in which $R_1$ and $R_2$ are identical, $R_4$ and $R_5$ are identical and are methyl or methoxy, $R_6$ is hydrogen or methyl, $R_7$ and $R_8$ are hydrogen, $R_9$ is $C_1$–$C_8$alkyl, methoxyethyl, ethoxyethyl, phenyl or benzyl, $R_{10}$ is hydrogen, $C_1$–$C_4$alkyl, especially methyl, or is $C_1$–$C_4$alkoxy, $R_{11}$ is hydrogen, $C_1$–$C_4$alkyl, especially methyl, or is $C_1$–$C_4$alkoxy, and $R_{12}$ is hydrogen.

Other preferred compounds of the formula I are those in which $R_4$ and $R_5$ independently of one another are $C_1$–$C_4$alkyl or $C_1$–$C_4$alkoxy, $R_6$ is hydrogen, $C_1$–$C_4$alkyl or $C_1$–$C_4$alkoxy, $R_7$ is hydrogen or methyl and $R_8$ is hydrogen.

The compounds of the formula I according to the invention can be prepared, for example, by double acylation of a primary phosphine (X) with at least 2 equivalents of an acid chloride (XI) in the presence of at least two equivalents of a base and subsequent oxidation of the resulting diacylphosphine (XII), in accordance with the scheme:

$$2\,R_1\text{—CO—Cl} + R_3\text{—PH}_2 \xrightarrow{\text{base}}$$

$$R_3\text{—P(CO—}R_1)_2 \xrightarrow{\text{oxidation}} R_3\text{—PO(CO—}R_1)_2$$
(XII) \hspace{2cm} (I)

$R_1$, $R_2$ and $R_3$ are as defined in claim 1.

Compounds of the formula I in which $R_1$ and $R_2$ are different are obtained by employing one equivalent each of an acid chloride $R_1$—CO—Cl and $R_2$—CO—Cl.

Compounds of the formula I in which $R_9$ is a radical of the formula IV or V are prepared as described above but replacing the primary phosphine (X) by "dimeric" phosphines (X' or X")

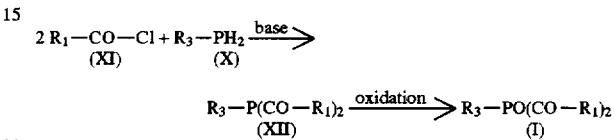

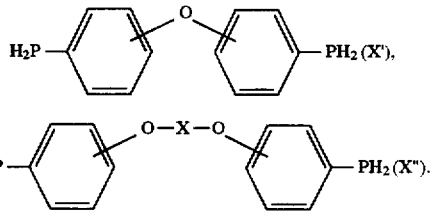

Examples of suitable bases are tertiary amines, pyridine, alkali metals, lithium diisopropylamide, butyllithium, alkaline earth metal carbonates, alkali metal alcoholates or alkali metal hydrides. The first step of the reaction is preferably carried out in solution. Particularly suitable solvents are hydrocarbons, for example alkanes and alkane mixtures, cyclohexane, benzene, toluene or xylene. Depending on the solvent and on the starting materials used, the reaction is carried out at various temperatures. When using bases such as lithium diisopropylamide or butyllithium it is advantageous to work at –40°–0° C. The reactions with tert-amines, alkali metals or alkali metal hydrides as bases are advantageously implemented, for example, at 10°–120° C., preferably 20°–80° C. After the base chloride formed has been separated off, the phosphine (XII) can be isolated by evaporative concentration. The crude reaction product can be used further without purification or else purified, for example, by crystallization. The second step of the reaction, however, can also be carried out without isolation of (XII), using the solution of the crude product. Suitable oxidizing agents for the second step, in order to prepare the oxides, are in particular hydrogen peroxide and organic peroxy compounds, for example peracetic acid or air.

The reaction products can be purified by generally conventional methods, for example by crystallization or chromatography.

The phosphines of the formula (X) (and correspondingly, those of the formulae X' and X" as well) can be prepared, for example, by hydrogenating the corresponding dichlorides (XIII) or phosphonic esters (XIV):

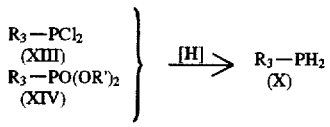

R' is for example methyl or ethyl.

The reactions are carried out under conditions which are generally known to those skilled in the art. The hydrogenation with LiAlH$_4$ can also be found, for example, from Helv. Chim. Acta 96 (1966), 842.

The dichlorides (XIII) can be obtained, for example, by Grignard reaction of the corresponding brominated aromatic compounds (XV) with PCl$_3$ (cf. e.g. Helv. Chim. Acta 35 (1952), 1412):

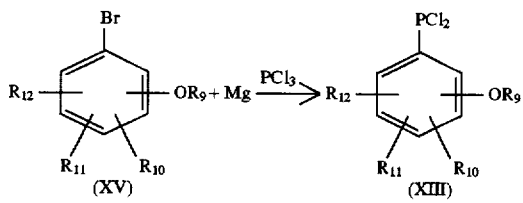

R$_9$, R$_{10}$, R$_{11}$ and R$_{12}$ are as defined in claim 1.

For the preparation of the "dimeric" phosphines (X' or X''), corresponding dibromides are used.

The diesters of formula (XIV) can be prepared, for example, by reacting the brominated aromatic compounds (XV) with a phosphorus triester (XVI). Such reactions are described for example in DE-C-1 810 431.

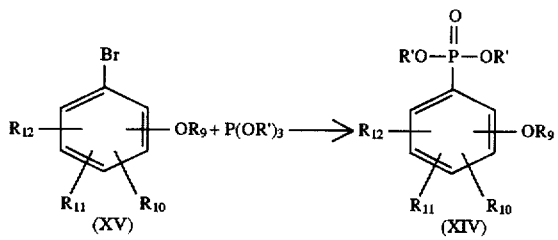

The brominated aromatic compounds (XV) are obtained by bromination reactions which are known in the prior art, for example by reacting alkoxylated aromatic compounds with N-bromosuccinimide or bromine/acetic acid.

The preparation of the acid chlorides of the formula (XI) is carried out by generally known methods from the prior art.

In accordance with the invention, the compounds of the formula I can be used as photoinitiators for the photopolymerization of ethylenically unsaturated compounds or of mixtures which comprise such compounds. This use may also be practised in combination with another photoinitiator and/or with other additives.

The invention therefore also relates to photopolymerizable compositions comprising (a) at least one ethylenically unsaturated photopolymerizable compound, and (b) as photoinitiator, at least one compound of the formula I.

In this context, the composition may contain other additives in addition to component (b), and component (b) may be a mixture of photoinitiators of the formula I and other photoinitiators.

The unsaturated compounds may contain one or more olefinic double bonds. They may be of low molecular weight (monomeric) or of relatively high molecular weight (oligomeric). Examples of monomers containing a double bond are alkyl or hydroxyalkyl acrylates or methacrylates, for example methyl, ethyl, butyl, 2-ethylhexyl or 2-hydroxyethyl acrylate, isobornyl acrylate, methyl methacrylate or ethyl methacrylate. Silicone acrylates are also of interest. Further examples are acrylonitrile, acrylamide, methacrylamide, N-substituted (meth)acrylamides, vinyl esters such as vinyl acetate, vinyl ethers such as isobutyl vinyl ether, styrene, alkylstyrenes and halostyrenes. N-vinylpyrrolidone, vinyl chloride or vinylidene chloride.

Examples of monomers containing two or more double bonds are the diacrylates of ethylene glycol, propylene glycol, neopentylglycol, hexamethylene glycol or bisphenol A, and also 4,4'-bis(2-acryloyloxyethoxy)diphenylpropane, trimethylolpropane triacrylate, pentaerythritol triacrylate or pentaerythritol tetraacrylate, vinyl acrylate, divinylbenzene, divinyl succinate, diallyl phthalate, triallyl phosphate, triallyl isocyanurate or tris(2-acryloylethyl) isocyanurate.

Examples of relatively high molecular weight (oligomeric) polyunsaturated compounds are acrylicized epoxy resins, and polyesters, polyurethanes and polyethers which are acrylicized or contain vinyl ether or epoxy groups. Further examples of unsaturated oligomers are unsaturated polyester resins which are mostly prepared from maleic acid, phthalic acid and one or more diols and have molecular weights of from about 500 to 3000. In addition it is also possible to employ vinyl ether monomers and vinyl ether oligomers, and also maleate-terminated oligomers having polyester, polyurethane, polyether, polyvinyl ether and epoxy main chains. Combinations of vinyl ether group-containing oligomers and polymers as are described in WO 90/01512 are particularly highly suitable. However, copolymers of vinyl ether and maleic acid-functionalized monomers are also appropriate. Such unsaturated oligomers can also be referred to as prepolymers.

Examples of particularly suitable compound are esters of ethylenically unsaturated carboxylic acids and polyols or polyepoxides, and polymers containing ethylenically unsaturated groups in the chain or in side groups, for example unsaturated polyesters, polyamides and polyurethanes and copolymers thereof, polybutadiene and butadiene copolymers, polyisoprene and isoprene copolymers, polymers and copolymers containing (meth)acrylic groups in side chains, and mixtures of one or more such polymers.

Examples of unsaturated carboxylic acids are acrylic acid, methacrylic acid, crotonic acid, itaconic acid, cinnamic acid, and unsaturated fatty acids such as linolenic acid or oleic acid. Acrylic acid and methacrylic acid are preferred.

Suitable polyols are aromatic and, in particular, aliphatic and cycloaliphatic polyols. Examples of aromatic polyols are hydroquinone, 4,4'-dihydroxybiphenyl, 2,2-di(4-hydroxyphenyl)propane, and also novolaks and resols. Examples of polyepoxides are those based on said polyols, especially aromatic polyols and epichlorohydrin. Other suitable polyols include polymers and copolymers which contain hydroxyl groups in the polymer chain or in side groups, for example polyvinyl alcohol and copolymers thereof or hydroxyalkyl polymethacrylates or copolymers thereof. Other suitable polyols are oligoesters containing hydroxyl end groups.

Examples of aliphatic and cycloaliphatic polyols are alkylenediols, preferably having 2 to 12 carbon atoms, such as ethylene glycol, 1,2- or 1,3-propanediol, 1,2-, 1,3- or 1,4-butanediol, pentanediol, hexanediol, octanediol, dodecanediol, diethylene glycol, triethylene glycol, polyethylene glycol having molecular weights of preferably from 200 to 1500, 1,3-cyclopentanediol, 1,2-, 1,3- or 1,4- cyclohexanediol, 1,4-dihydroxymethyl-cyclohexane, glycerol, tris-(β-hydroxyethyl)amine, trimethylolethane, trimethylolpropane, pentaerythritol, dipentaerythritol and sorbitol.

The polyols may be partially or fully esterified by means of one or more unsaturated carboxylic acids, where the free hydroxyl groups in partial esters may be modified, for example etherified or esterified with other carboxylic acids.

Examples of esters are:
trimethylolpropane triacrylate, trimethylolethane triacrylate, trimethylolpropane trimethacrylate, trimethylolethane trimethacrylate, tetramethylene glycol dimethacrylate, triethylene glycol dimethacrylate, tetraethylene glycol diacrylate, pentaerythritol diacrylate, pentaerythritol triacrylate, pentaerythritol tetraacrylate, dipentaerythritol diacrylate, dipentaerythritol triacrylate, dipentaerythritol tetraacrylate, dipentaerythritol pentaacrylate, dipentaerythritol hexaacrylate, tripentaerythritol octaacrylate, pentaerythritol dimethacrylate, pentaerythritol trimethacrylate, dipentaerythritoldimethacrylate, dipentaerythritol tetramethacrylate, tripentaerythritol octamethacrylate, pentaerythritol diitaconate, dipentaerythritol trisitaconate, dipentaerythritol pentaitaconate, dipentaerythritol hexaitaconate, ethylene glycol diacrylate, 1,3-butanediol diacrylate, 1,3-butanediol dimethacrylate, 1,4-butanediol diitaconate, sorbitol triacrylate, sorbitol tetraacrylate, pentaerythritol-modified triacrylate, sorbitol tetramethacrylate, sorbitol pentaacrylate, sorbitolhexaacrylate, oligoester acrylates and methacrylates, glycerol di- and triacrylate, 1,4-cyclohexane diacrylate, bisacrylates and bismethacrylates of polyethylene glycol having molecular weights of from 200 to 1500, or mixtures thereof.

Further suitable components (a) are the amides of identical or different unsaturated carboxylic acids of aromatic, cycloaliphatic and aliphatic polyamines, preferably having 2 to 6, in particular 2 to 4, amino groups. Examples of polyamines of this type are ethylenediamine, 1,2- or 1,3-propylenediamine, 1,2-, 1,3- or 1,4-butylenediamine, 1,5-pentylenediamine, 1,6-hexylenediamine, octylenediamine, dodecylenediamine, 1,4-diaminocyclohexane, isophoronediamine, phenylenediamine, bisphenylenediamine, di-β-aminoethyl ether, diethylenetriamine, triethylenetetrarine, di(β-aminoethoxy) or di(β-aminopropoxy)ethane. Other suitable polyamines are polymers and copolymers which may contain additional amino groups in the side chain, and oligoamides containing amino end groups. Examples of unsaturated amides of this type are: methylenebis-acrylamide, 1,6-hexamethylenebisacrylamide, bis diethylenetriaminetrismethacrylamide, bis (methacrylamidopropoxy)ethane, β-methacrylamidoethyl methacrylate, and N-[(β-hydroxyethoxy)ethyl] acrylamide.

Suitable unsaturated polyesters and polyamides are derived, for example, from maleic acid and diols or diamines. Some of the maleic acid may be replaced by other dicarboxylic acids. They can be employed together with ethylenically unsaturated comonomers, for example styrene. The polyesters and polyamides may also be derived from dicarboxylic acids and ethylenically unsaturated diols or diamines, in particular from relatively long chain compounds containing, for example, 6 to 20 carbon atoms. Examples of polyurethanes are those built up from saturated or unsaturated diisocyanates and from unsaturated or saturated diols.

Polybutadiene and polyisoprene and copolymers thereof are known. Examples of suitable comonomers are olefins such as ethylene, propene, butene, hexene, (meth)acrylate, acrylonitrile, styrene and vinyl chloride. Polymers containing (meth)acrylate groups in the side chain are also known. These may be, for example, products of the reaction of novolak-based epoxy resins with (meth)acrylic acid, homopolymers or copolymers of vinyl alcohol or hydroxyalkyl derivatives thereof which have been esterified using (meth)acrylic acid, or homopolymers and copolymers of (meth)acrylates which have been esterified using hydroxyalkyl (meth)acrylates.

The photopolymerizable compounds may be employed alone or in any desired mixtures. Preference is given to mixtures of polyol (meth)acrylates.

It is also possible to add binders to the compositions according to the invention; this is particularly expedient if the photopolymerizable compounds are liquid or viscous substances. The quantity of binder may be for example, 5–95% by weight, preferably 10–90% by weight and, in particular, 40–90% by weight, based on the overall solids content. The binder is chosen depending on the field of application and on the properties required therefor, such as the facility for development in aqueous and organic solvent systems, adhesion to substrates and sensitivity to oxygen.

Examples of suitable binders are polymers having a molecular weight of about 5000–2,000,000, preferably 10,000–1,000,000. Examples are homo- and copolymeric acrylates and methacrylates, for example copolymers of methyl methacrylate/ethyl acrylate/methacrylic acid, poly (alkyl methacrylates), poly(alkyl acrylates); cellulose esters and cellulose ethers, such as cellulose acetate, cellulose acetate butyrate, methylcellulose and ethylcellulose; polyvinylbutyral, polyvinylformal, cyclized rubber, polyethers, such as polyethylene oxide, polypropylene oxide and polytetrahydrofuran; polystyrene, polycarbonate, polyurethane, chlorinated polyolefins, polyvinyl chloride, copolymers of vinyl chloride/vinylidene chloride, copolymers of vinylidene chloride with acrylonitrile, methyl methacrylate and vinyl acetate, polyvinyl acetate, copoly (ethylene/vinyl acetate), polymers such as polycaprolactam and poly(hexamethyleneadipamide), and polyesters such as poly(ethylene glycol terephthalate) and poly(hexamethylene glycol succinate).

The unsaturated compounds may also be used in mixtures with non-photopolymerizable film-forming components. These may be, for example, physically drying polymers or solutions thereof in organic solvents, for example nitrocellulose or cellulose acetobutyrate. However, they may also be chemically curable or heat-curable resins such as, for example, polyisocyanates, polyepoxides or melamine resins. The additional use of heat-curable resins is important for use in so-called hybrid systems, which are photopolymerized in a first step and crosslinked by thermal aftertreatment in a second step.

The photopolymerizable mixtures may contain various additives in addition to the photoinitiator. Examples thereof are thermal inhibitors, which are intended to prevent premature polymerization, for example the hydroquinone, hydroquinine derivatives, p-methoxyphenol, β-naphthol or sterically hindered phenols such as 2,6-di(tert-butyl)-p-cresol. The shelf life in the dark can be increased, for example, by using copper compounds such as copper naphthenate, copper stearate or copper octanoate, phosphorus compounds, for example triphenylphosphine, tributylphosphine, triethyl phosphite, triphenyl phosphite or tribenzyl phosphite, quaternary ammonium compounds, for example tetramethylammonium chloride or trimethylbenzylammonium chloride, or hydroxylamine derivatives, for example N-diethylhydroxylamine. In order to exclude atmospheric oxygen during the polymerization, paraffin or similar wax-like substances can be added; these migrate to the surface on commencement of the polymerization because of their low solubility in the polymer, and form a transparent surface layer which prevents the ingress of air. Light stabilizers which can be added in small quantities are UV absorbers, for example those of the benzotriazole, benzophenone, oxalanilide or hydroxyphenyl-s-triazine type. These compounds can be employed individually or as mixtures, with or without the use of sterically hindered amines (HALS).

Examples of such UV absorbers and light stabilizers are:
1. 2-(2'-Hydroxyihenyl)benzotriazoles, for example 2-(2'-hydroxy-5'-methylphenyl)benzotriazole, 2-(3',-di-tert-butyl-2'-hydroxyphenyl)benzotriazole, 2-(5'-tert-butyl-2'-hydroxyphenyl)benzotriazole, 2-(2'-hydroxy-5'-(1,1,3,3-tetramethylbutyl)phenyl)benzotriazole, 2-(3',5'-di-tert-butyl-2'-hydroxyphenyl)-5-chlorobenzotriazole, 2-(3'-tert-butyl- 2'-hydroxy-5'-methylphenyl)-5-chlorobenzotriazole, 2-(3'-sec-butyl-5'-tert-butyl-2'-hydroxy-phenyl)benzotriazole, 2-(2'-hydroxy-4'-octoxyphenyl)benzotriazole, 2-(3',5'di-tert-amyl-2'-hydroxyphenyl)benzotriazole, 2-(3',5'-bis(α,α-dimethylbenzyl)-2'-hydroxyphenyl)benzotriazole, mixture of 2-(3'-tert-butyl-2'-hydroxy-5'-(2-octyloxycarbonylethyl)phenyl)-5-chlorobenzotriazole, 2-(3'-tert-butyl-5'-[2-(2-ethylhexyloxy)carbonylethyl]-2'-hydroxyphenyl)-5-chlorobenzotriazole, 2-(3'-tert-butyl-2'-hydroxy-5'-(2-methoxycarbonylethyl)phenyl)-5-chlorobenzotriazole, 2-(3'-tert-butyl-2'-hydroxy-5'-(2-methoxycarbonylethyl)phenyl) benzotriazole, 2-(3'-tert-butyl-2'-hydroxy-5'-(2-octyloxycarbonylethyl)phenyl)benzotriazole, 2-(3'-tert-butyl-5 '-[2-(2-ethylhexyloxy)carbonylethyl]-2'-hydroxyphenyl)benzotriazole, 2-(3'-dodecyl-2'-hydroxy-5'-methylphenyl)benzotriazole, and 2-(3'-tert-butyl-2'-hydroxy- 5'-(2-isooctyloxycarbonylethyl) phenylbenzotriazole, 2,2'-methylenebis[4-(1,1,3,3-tetramethylbutyl)-6-benzotriazol-2-yl phenol]; transesterification product of 2-[3'-tert-butyl-5'-(2-methoxycarbonylethyl)-2'-hydroxyphenyl)benzotriazole with polyethylene glycol 300; [R—CH$_2$CH$_2$—COO(CH$_2$)$_3$]$_2$ where R=3'-tert-butyl-4'-hydroxy-5'-2H-benzotriazol-2-yl phenyl.

2. 2-Hydroxvbenzophenones, for example the 4-hydroxy, 4-methoxy, 4-octoxy, 4-decyloxy, 4-dodecyloxy, 4-benzyloxy, 4,2',4'-trihydroxy and 2'-hydroxy-4,4'-dimethoxy derivatives.

3. Esters of unsubstituted or substituted benzoic acids, for example 4-tert-butyl-phenyl salicylate, phenyl salicylate, octylphenyl salicylate, dibenzoylresorcinol, bis(4-tert-butylbenzoyl)resorcinol, benzoylresorcinol, 2,4-di-tert-butylphenyl 3,5-tert-butyl-4-hydroxybenzoate, hexadecyl 3,5-di-tert-butyl4-hydroxybenzoate, octadecyl 3,5-di-tert-butyl-4-hydroxybenzoate, 2-methyl-4,6-di-tert-butylphenyl 3,5 di-tert-butyl-4-hydroxybenzoate.

4. Acrylates, for example ethyl and isooctyl α-cyano-β,β-diphenylacrylate, methyl a-carbomethoxycinnamate, methyl and butyl α-cyano-βo-methyl-p-methoxycinnamate, methyl α-carbomethoxy-p-methoxycinnamate and N-(β-carbomethoxy-β-cyanovinyl)-2-methylindoline.

5. Sterically hindered amines, for example bis(2,2,6,6-tetramethylpiperidyl) sebacate, bis(2,2,6,6-tetramethylpiperidyl) succinate, bis(1,2,2,6,6-pentamethylpiperidyl) sebacate, bis(1,2,2,6,6-pentamethylpiperidyl) n-butyl-3,5-di-tert-butyl-4-hydroxybenzylmalonate, the product of the condensation of 1-hydroxyethyl-2,2,6,6-tetramethyl-4-hydroxypiperidine and succinic acid, the product of the condensation of N,N'-bis(2,2,6,6-tetramethyl-4-piperidyl)hexamethylenediamine and 4-tert-octylamino-2,6-dichloro-1,3,5-s-triazine, tris(2,2,6,6- tetramethyl-4-piperidyl) nitrilotriacetate, tetrakis(2,2,6,6-tetramethyl-4-piperidyl) 1,2,3,4-butanetetraoate, 1,1'-(1,2-ethanediyl)bis-(3,3,5,5-tetramethylpiperazinone), 4-benzoyl-2,2,6,6-tetramethylpiperidine, 4-stearyloxy-2,2,6,6-tetramethylpiperidine, bis(1,2,2,6,6-pentamethylpiperidyl) 2-n-butyl-2-(2-hydroxy-3,5-di-tert-butylbenzyl)malonate, 3-n-octyl-7,7,9,9-tetramethyl-1,3,8-triazaspiro[4,5]decane-2,4-dione, bis(1-octyloxy-2,2,6,6-tetramethylpiperidyl) sebacate, bis(1-octyloxy-2,2,6,6-tetramethylpiperidyl) succinate, the product of the condensation of N,N'-bis(2,2,6,6-tetramethyl-4-piperidyl) hexamethylene diamine and 4-morpholino-2,6-dichloro-1,3,5-triazine, the product of the condensation of 2-chloro-4,6-di(4-n-butylamino-2,2,6,6-tetramethyl-piperidyl)1,3,5-triazine and 1,2-bis(3-aminopropylamino)ethane, the product of the condensation of 2-chloro-4,6-di(4-n-butylamino-1,2,2,6,6-pentamethylpiperidyl)-1,3,5-triazine and 1,2-bis(3-aminopropylamino)ethane, 8-acetyl-3-dodecyl-7,7,9,9-tetra-methyl- 1,3,8-triazaspiro[4,5]decane-2,4-dione, 3-dodecyl-1 -(2,2,6,6-tetramethyl-4-piperidyl) pyrrolidine-2,5-dione, 3-dodecyl-1-(1,2,2,6,6-pentamethyl-4-piperidyl)pyrrolidine-2,5-dione.

6. Oxalamides, for example 4,4'-dioctyloxyoxanilide, 2,2'-diethoxyoxanilide, 2,2'-dioctyloxy-5,5'-di-tert-butyloxanilide, 2,2'-didodecyloxy-S,5'-di-tert-butyloxanilide, 2-ethoxy-2'-ethyloxanilide, N,N'-bis(3-dimethylaminopropyl)oxalamide, 2-ethoxy-S-tert-butyl-2'-ethyloxanilide and mixtures thereof with 2-ethoxy-2'-ethyl-5,4'-di-tert-butyloxanilide, and mixtures of o- and p-methoxy- and of o- and p-ethoxy-disubstituted oxanilides.
7. 2-(2-Hydroxyphenyl)-1,3,5-triazines, for example 2,4,6-tris(2-hydroxy-4-octyloxyphenyl)-1,3,5-triazine, 2-(2-hydroxy-4-octyloxyphenyl)-4,6-bis(2,4-dimethylphenyl)-1,3,5-triazine, 2-(2,4-dihydroxyphenyl)-4,6-bis(2,4-dimethylphenyl)-1,3,5-triazine, 2,4-bis(2-hydroxy4-propyloxyphenyl)-6-(2,4-dimethylphenyl)-1,3,5-triazine, 2-(2-hydroxy4-octyloxyphenyl)-4,6-bis(4-methylphenyl)-1,3,5-triazine, 2-(2-hydroxy-4-dodecyloxyphenyl)-4,6-bis(2,4-dimethylphenyl)-1,3,5-triazine, 2-[2-hydroxy4-(2-hydroxy-3-butyloxypropyloxy)phenyl]-4,6-bis(2,4-dimethylphenyl)-1,3,5-triazine, 2-[2-hydroxy-4-(2-hydroxy-3-octyloxy-propyloxy)phenyl]-4,6-bis(2,4-dimethylphenyl)-1,3,5-triazine and 2-[4-dodecylltridecyloxy(2-hydroxypropyl)oxy-2-hydroxyphenyl]-4,6-bis(2,4-dimethyl-phenyl)-1,3,5-triazine.

8. Phosphites and phosphonites, for example triphenyl phosphite, diphenyl alkyl phosphites, phenyl dialkyl phosphites, tris(nonylphenyl) phosphite, trilauryl phosphite, trioctadecyl phosphite, distearyl pentaerythrityl diphosphite, tris(2,4-di-tert-butylphenyl) phosphite, diisodecylpentaerythrityl diphosphite, bis(2,4-di-tert-butylphenyl) pentaerythrityl diphosphite, bis(2,6-di-tert-butyl-4-methylphenyl) pentaerythrityl diphosphite, bisisodecyloxypentaerythrityl diphosphite, bis(2,4-di-tert-butyl-6-methylphenyl) pentaerythrityl diphosphite, bis(2,4,6-tri-tert-butylphenyl) pentaerythrityl diphosphite, tristearyl sorbityl triphosphite, tetrakis(2,4-di-tert-butylphenyl)-4,4'-biphenylenediphosphonite, 6-isooctyloxy-2,4,8,10-tetra-tert-butyl-12H-dibenz[d,g]-1,3,2-dioxaphosphocine, 6-fluoro-2,4,8, 10-tetra-tert-butyl-12-methyl-dibenz[d,g]-1,3,2-dioxaphosphocine, bis(2,4-di-tert-butyl-6-methylphenyl)methyl phosphite, and bis(2,4-di-tert-butyl-6-methylphenyl) ethyl phosphite.

To accelerate the photopolymerization it is possible to add amines such as, for example, triethanolamine, N-methyldiethanolamine, ethyl p-dimethylaminobenzoate or Michler's ketone. The action of the amines can be intensified by the addition of aromatic ketones of the benzophenone type. Examples of amines which can be used as oxygen scavengers are substituted N,N-dialkylanilines as described in EP-A-339 841.

The photopolymerization can also be accelerated by addition of photosensitizers which shift or broaden the spectral sensitivity. These are, in particular, aromatic carbonyl compounds such as benzophenone derivatives, thioxanthone derivatives, anthraquinone derivatives and 3-acylcoumarin derivatives and 3-(aroylmethylene)thiazolines, and also eosin, rhodanine and erythrosine dyes. The curing process may be assisted, in particular, by compositions pigmented with $TiO_2$, for example, but also by addition of a component which forms free radicals under thermal conditions, for example an azo compound such as 2,2'-azobis(4-methoxy-2,4-dimethylvaleronitrile) or a peroxy compound such as a hydroperoxide or peroxycarbonate, for example t-butyl hydroperoxide, as described in EP-A 245 639, for example.

The compositions according to the invention may also contain a photoreducible dye, for example a xanthene, benzoxanthene, benzothioxanthene, thiazine, pyronine, porphyrin or acridine dyes, and/or a trihalomethyl compound which can be cleaved by radiation. Similar compositions are described in, for example, EP-A-445 624.

Other conventional additives are—depending on the application—optical brighteners, fillers, pigments, dyes, wetting agents or levelling assistants. Thick and pigmented coatings can suitably be cured by the addition of glass microbeads or powdered glass fibres, as described in U.S. Pat. No. 5 013 768, for example.

The invention also relates to compositions comprising as component (a) at least one ethylenically unsaturated, photopolymerizable compound which is emulsified or dissolved in water.

Radiation-curable, aqueous prepolymer dispersions of this type are commercially available in many variations. This term is taken to mean a dispersion of water and at least one prepolymer dispersed therein. The concentration of the water in these systems is, for example, from 5 to 80% by weight, in particular from 30 to 60% by weight. The radiation-curable prepolymer or prepolymer mixture is present, for example, in concentrations of from 95 to 20% by weight, in particular from 70 to 40% by weight. The total of the percentages indicated for water and prepolymer in these compositions is in each case 100, to which are added the assistants and additives in various amounts depending on the application.

The radiation-curable, water-dispersed, film-forming prepolymers, which are frequently also dissolved, are, for aqueous prepolymer dispersions, monofunctional or polyfunctional ethylenically unsaturated prepolymers which are known per se, can be initiated by means of free radicals and contain, for example, from 0.01 to 1.0 mol of polymerizable double bonds per 100 g of prepolymer, and have an average molecular weight of, for example, at least 400, in particular from 500 to 10,000. Depending on the intended application, however, prepolymers having higher molecular weights may also be suitable. For example, polyesters containing polymerizable C—C double bonds and having a maximum acid number of 10, polyethers containing polymerizable C—C double bonds, hydroxyl-containing products of the reaction of a polyepoxide containing at least two epoxide groups per molecule with at least one α,β-ethylenically unsaturated carboxylic acid, polyurethane (meth)acrylates and α,β-ethylenically unsaturated acrylic copolymers containing acrylic radicals, as described in EP-A-12 339, are used. Mixtures of these prepolymers may also be used. Also suitable are the polymerizable prepolymers described in EP-A-33 896, which are thioether adducts of polymerizable prepolymers having an average molecular weight of at least 600, a carboxyl group content of from 0.2 to 15% and a content of from 0.01 to 0.8 mol of polymerizable C—C double bonds per 100 g of prepolymer. Other suitable aqueous dispersions based on specific alkyl (meth)acrylate polymers are described in EP-A-41 125, and suitable water-dispersible, radiation-curable prepolymers made from urethane acrylates are disclosed in DE-A-2 936 039.

These radiation-curable, aqueous prepolymer dispersions may contain, as further additives, dispersion assistants, emulsifiers, antioxidants, light stabilizers, dyes, pigments, fillers, for example talc, gypsum, silica, rutile, carbon black, zinc oxide and iron oxides, reaction accelerators, levelling agents, lubricants, wetting agents, thickeners, matting agents, antifoams and other assistants which are conventional in surface-coating technology. Suitable dispersion assistants are water-soluble, high molecular weight organic compounds containing polar groups, for example polyvinyl alcohols, polyvinylpyrrolidone and cellulose ethers. Emulsifiers which can be used are nonionic emulsifiers and possibly also ionic emulsifiers.

In certain cases it may be of advantage to use mixtures of two or more of the photoinitiators according to the invention. It is of course also possible to use mixtures with known photoinitiators, for example mixtures with benzophenone, acetophenone derivatives, for example α-hydroxycycloalkylphenyl ketones, dialkoxyacetophenones, α-hydroxy- or α-aminoacetophenones, 4-aroyl-1,3-dioxolanes, benzoin alkyl ethers and benzil ketals, monoacylphosphine oxides, bisacylphosphine oxides or titanocenes. When the photoinitiators according to the invention are employed in hybrid systems, cationic photoinitiators such as aromatic sulfonium or iodonium salts or cyclopentadienylareneiron (II) complex salts are used in addition to the free-radical curing agents according to the invention.

The photopolymerizable compositions contain the photoinitiator or the photoinitiator mixture (b) advantageously in a quantity of from 0.05 to 15% by weight, preferably from 0.1 to 5% by weight, based on the composition.

The invention also relates to compositions in which the additional photoinitiators are compounds of the formula (VII)

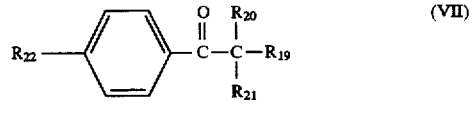

or (VII)

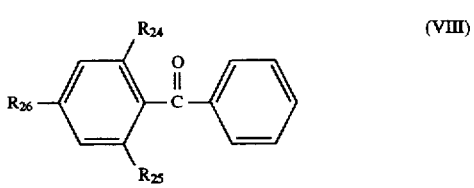

or mixtures of compounds of the formulae (VII) and (VIII), in which $R_{19}$ and $R_{20}$ independently of one another are hydrogen, $C_1$–$C_6$alkyl, phenyl, $C_1$–$C_{16}$alkoxy or -O(CH$_2$CH$_2$O)q-

$C_1$–$C16$alkyl, in which q is a number from 1–20, or $R_{19}$ and $R_{20}$, together with the carbon atom to which they are attached, form a cyclohexyl ring, $R_{21}$ is hydroxyl, $C_1$–$C_{16}$alkoxy or —O($CH_2CH_2O)_q$—$C_1$–$C_{16}$alkyl, where $R_{20}$, $R_{21}$ and $R_{22}$ are not all simultaneously $C_1$–$C_{16}$alkoxy or —O($CH_2CH_2O)_q$—$C_1$–$C_{16}$alkyl, $R_{22}$ is hydrogen, $C_1$–$C_{18}$alkyl, $C_1$–$C_{18}$alkoxy, —OCH$_2$CH$_2$—OR$_{23}$,

or a group

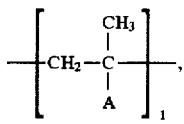

in which 1 has a value from 2 to 10 and A is the radical

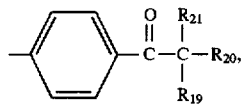

$R_{23}$ is hydrogen,

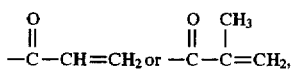

and $R_{24}$, $R_{25}$ and $R_{26}$ independently of one another are hydrogen or methyl.

$R_{22}$ as $C_1$–$C_{18}$alkyl and also $R_{20}$ and $R_{21}$ as $C_1$–$C_6$alkyl, may have the same meanings as those described for $R_1$, up to the respective number of carbon atoms.

$R_{22}$ as $C_1$–$C_{18}$alkoxy is for example branched or unbranched alkoxy, for example methyloxy, ethyloxy, n-propyloxy, isopropyloxy, n-butyloxy, isobutyloxy, sec-butyloxy, tert-butyloxy, pentyloxy, hexyloxy, heptyloxy, octyloxy, 2,4,4-trimethyl-1-pentyloxy, 2-ethylhexyloxy, nonyloxy, decyloxy, dodecyloxy or octadecyloxy.

$R_{19}$, $R_{20}$ and $R_{21}$ as $C_1$–$C_{16}$alkoxy may have the same meanings as those described for $R_{22}$, up to the appropriate number of carbon atoms, and are preferably decyloxy, methoxy and ethoxy, especially methoxy and ethoxy.

The radical —O($CH_2CH_2O)_q$—$C_1$–$C_{16}$alkyl represents 1 to 20 successive ethylene oxide units whose chain ends in $C_1$–$C_{16}$alkyl. q is preferably 1 to 10, for example 1 to 8, especially 1 to 6. The chain of ethylene oxide units is preferably terminated with a $C_1$–Cloalkyl, for example $C_1$–$C_8$alkyl, especially $C_1$–$C_4$alkyl.

Preferred compositions are those in which, in the formula (VII), $R_{20}$ and $R_{21}$ independently of one another are $C_1$–$C_6$alkyl, or together with the carbon atom to which they are attached form a cyclohexyl ring, and $R_{19}$ is hydroxyl.

Further preferred compositions are those in which the proportion of compounds of the formula (I) in a mixture with compounds of the formulae (VII) and/or (VIII) is from 5 to 95%, preferably from 5 to 50%.

Also important are compositions in which, in the compounds of the formula (VII), $R_{20}$ and $R_2$, are identical and are methyl, and $R_{19}$ is hydroxyl or isopropoxy.

Preference is likewise given to compositions comprising compounds of the formula (I) and a mixture of compounds of the formula (VIII), in which compounds of the formula (VIII) where $R_{25}$ and $R_{26}$ are both hydrogen and $R_{24}$ is methyl are present to the extent of 20%, and compounds of the formula (VIII) where $R_{25}$, $R_{24}$ and $R_{26}$ are all methyl are present to the extent of 80%.

Very special interest attaches to compounds as described above which comprise photoinitiator mixtures of the formulae (I), (VII) and/or (VIII), and which are liquid at room temperature.

The preparation of the compounds of the formulae (VII) and (VIII) is generally known, and some of the compounds are commercially available. The preparation of oligomeric compounds of the formula (VII) is described, for example, in EP-A-161 463. A description of the preparation of compounds of the formula (VIII) can be found, for example, in EP-A-209 831.

The photopolymerizable compositions can be used for various purposes, for example as printing inks, as varnishes or clearcoats, as white paints, for example for wood or metal, as coating subtances, inter alia, for paper, wood, metal or plastic, as daylight-curable coatings for buildings and roadmarking, for photographic reproduction processes, for holographic recording materials, for image recording processes or for the production of printing plates which can be developed using organic solvents or aqueous-alkaline media, for the production of masks for screen printing, as dental filling materials, as adhesives, as pressure-sensitive adhesives, as laminating resins, as etch resists or permanent resists and as solder masks for electronic circuits, for the production of threedimensional articles by bulk curing (UV curing in transparent moulds) or by the stereolithography process, as described, for example, in U.S. Pat. No. 4 575 330, for the preparation of composite materials (for example styrenic polyesters, which may contain glass fibres and other assistants) and other thick-layer compositions, for the coating or encapsulation of electronic components or as coatings for optical fibres. The compounds according to the invention may also be used as initiators for emulsion polymerizations, as initiators of a polymerization for the fixing of ordered states of liquid-crystalline mono- and oligomers, as initiators for the fixing of dyes to organic materials, and for curing powder coatings.

In coating materials, mixtures of a prepolymer with polyunsaturated monomers are often used which also contain a monounsaturated monomer. The prepolymer here is primarily responsible for the properties of the coating film, a ation thereof allows the person skilled in the art to influence the properties of the cured film. The polyunsaturated monomer functions as a crosslinking agent which renders the coating film insoluble. The monounsaturated monomer functions as a reactive diluent by means of which the viscosity is reduced without the need to use a solvent.

Unsaturated polyester resins are mostly used in two-component systems in conjunction with a monounsaturated monomer, preferably styrene. For photoresists, specific one-component systems are frequently employed, for example polymaleimides, polychalcones or polyimides, as described in DE-A-23 08 830.

The compounds according to the invention and mixtures thereof may also be used as free-radical photoinitiators or photoinitiating systems for radiation-curable powder coatings. The powder coatings may be based on solid resins and monomers containing reactive double bonds, for example maleates, vinyl ethers, acrylates, acrylamides and mixtures thereof. A free-radically UV-curable powder coating can be formulated by mixing unsaturated polyester resins with solid acrylamides (e.g. methyl methacrylamidoglycolate) and with a free-radical photoinitiator according to the invention, as described, for example, in the paper "Radiation Curing of Powder Coating", Conference Proceedings, Radtech Europe 1993 by M. Wittig and Th. Gohmann. Similarly, free-radically UV-curable powder coatings can be formulated by mixing unsaturated polyester resins with solid acrylates, methacrylates or vinyl ethers and with a photoinitiator (or mixture of photoinitiators) according to the invention. The powder coatings may also contain binders as described for example in DE-A-42 28 514 or EP-A-636 669. The UV-curable powder coatings may also comprise white or coloured pigments. Thus, for example, preferably rutile titanium dioxide can be employed in concentrations of up to 50% by weight in order to give a cured powder coating having good covering power. The process normally comprises electrostatic or tribostatic spraying of the powder onto the substrate, for example of metal or wood, melting the powder by heating and, after a smooth film has been formed, radiation-curing of the coating using ultraviolet and/or visible light, for example with medium-pressure mercury lamps, metal halide lamps or xenon lamps. A particular advantage of the radiation-curable powder coatings over their heat-curable counterparts is that the flow time after the melting of the powder particles can be selectively extended in order to ensure the formation of a smooth, high-gloss coating. In contrast to heat-curable systems, radiation-curable powder coatings can be formulated without the unwanted effects of a reduction in their lifetime so that they melt at relatively low temperatures. For this reason, they are also suitable as coatings for heat-sensitive substrates such as wood or plastics.

In addition to the photoinitiators according to the invention, the powder coating formulations may also contain UV absorbers. Appropriate examples have been listed above under items 1–8.

The photocurable compositions according to the invention are suitable, for example, as coating substances for substrates of all kinds, for example wood, textiles, paper, ceramic, glass, plastics such as polyesters, polyethylene terephthalate, polyolefins or cellulose acetate, especially in the form of films, and also metals such as Al, Cu, Ni, Fe, Zn, Mg or Co and GaAs, Si or $SiO_2$, on which it is desired to apply a protective coating or, by imagewise exposure, an image.

The substrates can be coated by applying a liquid composition, a solution or suspension to the substrate. The choice of the solvent and the concentration depend predominantly on the type of composition and the coating procedure. The solvent should be inert: in other words it should not undergo any chemical reaction with the components and should be capable of being removed again after the coating operation, in the drying process. Examples of suitable solvents are ketones, ethers and esters, such as methyl ethyl ketone, isobutyl methyl ketone, cyclopentanone, cyclohexanone, N-methylpyrrolidone, dioxane, tetrahydrofuran, 2-methoxyethanol, 2-ethoxyethanol, 1-methoxy-2-propanol, 1,2-dimethoxyethane, ethyl acetate, n-butyl acetate and ethyl 3-ethoxypropionate. Using known coating processes, the solution is applied evenly to a substrate, for example by spincoating, dip coating, knife coating, curtain coating, brushing, spraying, especially electrostatic spraying, and reverse roll coating. It is also possible to apply the photosensitive layer to a temporary, flexible support and then to coat the final substrate, for example a copper-laminated circuit board, by means of layer transfer via lamination.

The quantity applied (layer thickness) and the nature of the substrate (layer support) are functions of the desired application. The range of coat thicknesses generally comprises values from about 0.1 µm to more than 10 µm.

The radiation-sensitive compositions according to the invention find application as negative resists which have a very high photosensitivity and can be developed in an aqueous-alkaline medium without swelling. They are suitable as photoresists for electronics (galvanoresists, etch resists and solder resists), the production of printing plates such as offset printing plates or screen printing formes, and can be used for chemical milling or as microresists in the production of integrated circuits. There is a correspondingly wide range of variation in the possible layer supports and the processing conditions for the coated substrates.

Examples of the layer supports for photographic information recordings are films made of polyester, cellulose acetate or plastic-coated papers; for offset printing plates, specially treated aluminium; for the production of printed circuits, copper-faced laminates; and for the production of integrated circuits, silicon wafers. The layer thicknesses for photographic materials and offset printing plates are generally from about 0.5 µm to 10 µm, while for printed circuits they are from 0.4 µm to about 2 µm. Following the coating of the substrates, the solvent is generally removed by drying to leave a layer of the photoresist on the substrate.

The term "imagewise exposure" relates both to exposure through a photomask containing a predetermined pattern, for example a slide, exposure by a laser beam which is moved under control from a computer, for example, over the surface of the coated substrate, thereby generating an image, and irradiation with computer-controlled electron beams. Following the imagewise exposure of the material and prior to developing, it may be advantageous to carry out a brief thermal treatment, in which only the exposed parts are thermally cured. The temperatures employed are generally 50°–150° C. and preferably 80°–130° C.; the duration of the thermal treatment is generally between 0.25 and 10 minutes. The photocurable composition can also be used in a process for the production of printing plates or photoresists as described, for example, in DE-A-40 13 358. In this process the composition is exposed before, simultaneously with or after the imagewise irradiation, exposure being carried out for a short period with visible light at a wavelength of at least 400 nm without a mask.

Following the exposure and the optional thermal treatment, the unexposed areas of the photoresist are removed using a developer in a manner known per se.

As already mentioned, the compositions according to the invention can be developed by aqueous-alkaline media. Suitable aqueous-alkaline developer solutions are, in particular, aqueous solutions of tetraalkylammonium hydroxides or of alkali metal silicates, phosphates, hydroxides and carbonates. Relatively small quantities of wetting agents and/or organic solvents may also be added, if desired, to these solutions. Examples of typical organic solvents which may be added in small quantities to the developing liquids are cyclohexanone, 2-ethoxyethanol, toluene, acetone and mixtures of such solvents.

Photocuring is of considerable importance for printing inks, since the drying time of the binder is a crucial factor for the production rate of graphic products and should be in the order of fractions of seconds. UV-curable inks are important, in particular, for screen printing.

As already mentioned, the mixtures according to the invention are also highly suitable for the production of printing plates, where, for example, mixtures of soluble, linear polyamides or styrene/butadiene or styrene/isoprene rubber, polyacrylates or polymethyl methacrylates containing carboxyl groups, polyvinyl alcohols or urethane acrylates are used with photopolymerizable monomers, for example acrylamides, methacrylamides, acrylates or methacrylates, and a photoinitiator. Films and plates made from these systems (wet or dry) are exposed through the negative (or positive) of the print original, and the uncured parts are subsequently washed out using a suitable solvent.

A further area of application for photocuring is the coating of metals, for example in the coating of metal sheets and tubes, cans or bottle caps, and the photocuring of plastic coatings, for example PVC-based wall or floor coverings.

Examples of the photocuring of paper coatings are the colourless coating of labels, record sleeves or book covers.

The use of the compounds according to the invention for curing shaped articles made from composite compositions is likewise of interest. The composite composition is made up of a self-supporting matrix material, for example a glass-fibre fabric, or else, for example, plant fibres [cf. K.-P. Mieck and T. Reussmann in Kunststoffe 85 (1995), 366–370], which is impregnated with the photocuring formulation. Shaped articles which are produced from composite compositions, using the compounds according to the invention, are of high mechanical stability and resistance. The compounds according to the invention can also be employed as photocuring agents in moulding, impregnating and coating compositions, as described, for example, in EP-A-7086. Examples of such compositions are fine coating resins on which stringent requirements are placed with respect to their curing activity and yellowing resistance, or fibre-reinforced mouldings such as planar or longitudinally or transversely corrugated light diffusing panels. Processes for the production of such mouldings, for example hand lay-up, spray lay-up, centrifugal or filament winding processes, are described by, for example P.H. Selden in "Glasfaserverstarkte Kunststoffe" [Glass fibre-reinforced plastics], page 610, Springer Verlag Berlin-Heidelberg-New York 1967. Examples of articles for use which can be produced by this process are boats, chipboard or plywood panels coated on both sides with glass fibre-reinforced plastic, pipes, containers and the like. Other examples of moulding, impregnating and coating compositions are UP resin fine coatings for mouldings containing glass fibres (GRP), e.g. corrugated sheets and paper laminates. Paper laminates may also be based on urea or melamine resins. The fine coating is produced on a support (for example a film) prior to the production of the laminate. The photocurable compositions according to the invention can also be used for casting resins or for encapsulating articles such as electronic components and the like. Curing employs medium-pressure mercury lamps as are conventional in UV curing. However, less intense lamps are also of particular interest, for example those of the type TL40W/03 or TL40W/05. The intensity of these lamps corresponds approximately to that of sunlight. Direct sunlight can also be used for curing. A further advantage is that the composite composition can be removed from the light source in a partially cured, plastic state and can be deformed. Curing is subsequently carried out to completion.

Also important is the use of photocurable compositions for imaging processes and for the optical production of information carriers. In these applications, the coat (wet or dry) applied to the support is irradiated—as already described above—with UV or visible light through a photomask and the unexposed areas of the coat are removed by treatment with a solvent (=developer). The photocurable layer can also be applied by electrodeposition to metal. The exposed areas are crosslinkedipolymeric and thus insoluble and remain on the support. If appropriate colouration is carried out, visible images are formed. If the support is a metallized layer, then the metal can be removed from the unexposed areas by etching after exposure and development or can be increased in thickness by electroplating. In this way, printed electronic circuits and photoresists can be produced.

The photosensitivity of the compositions according to the invention generally ranges from the UV region (about 200 nm) up to about 600 nm, and therefore spans a very wide range. Suitable radiation comprises, for example, sunlight or light from artificial sources. Therefore, a large number of very different types of light source can be used. Both point sources and flat radiators (lamp carpets) are appropriate. Examples are: carbon arc lamps, xenon arc lamps, medium-pressure, high-pressure and low-pressure mercury lamps, doped with metal halides if desired (metal halogen lamps), microwave-stimulated metal vapour lamps, excimer lamps, superactinic fluorescent tubes, fluorescent lamps, incandescent argon lamps, electronic flashlights, photographic flood lamps, electron beams and X-rays, produced by means of synchrotrons, or laser plasma. The distance between the lamp and the substrate according to the invention which is to be exposed can vary depending on the application and on the type and/or power of the lamp, for example from between 2 cm and 150 cm. Of particular suitability are laser light sources, for example excimer lasers, such as krypton F lasers for exposure at 248 nm. Lasers in the visible range may also be employed. In this case the high sensitivity of the materials according to the invention is very advantageous. By this method it is possible to produce printed circuits in the electronics industry, lithographic offset printing plates or relief printing plates, and photographic image recording materials.

The term daylight or daylight-equivalent light sources refers to radiation of wavelength 300–500 nm. In this context, radiation of wavelength 400–450 nm, in particular, must be present for curing. In contrast to the conventional UV curing with high-intensity radiation, in daylight curing the curing effect is achieved by the action of lower-intensity radiation over a longer period. Examples of such radiation are sunlight, and radiation sources which are equivalent to daylight Sunlight differs from the light from the artificial radiation sources which are usual and customary in UV curing in respect of its spectral composition and intensity. The absorption characteristics and the radical-forming properties of the bisacylphosphine oxides employed in the process according to the invention are particularly suitable for utilizing sunlight as natural radiation source for the curing.

The dimeric bisacylphosphine oxides employed in the process according to the invention give tack-free surfaces within 1–30, in particular 1–15 minutes on irradiation with daylight or with daylight-equivalent light sources. The radiation intensities of the radiation which can be utilized for curing are in the range of 25–35 W/cm$^2$. The term daylight-equivalent artificial light sources, as may be used to cure compounds according to the invention, refers to low-intensity radiators such as, for instance, certain fluorescent lamps, e.g. the TL03, TL15 or TL09 Philips special fluorescent lamps.

The invention therefore also relates to the use of compounds of the formula I in which $R_3$ is a group of the formula IIIb

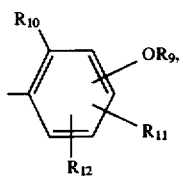

(IIIb)

in which

R$_9$ is C$_1$-C$_{12}$alkyl, C$_2$-C$_{12}$alkyl which is interrupted by O, or is C$_1$-C$_4$alkyl which is substituted with C$_3$-C$_8$alkenoxy, or is cyclopentyl, cyclohexyl, phenyl which is unsubstituted or is substituted with 1–4 C$_1$-C$_4$alkyl and/or C$_1$-C$_4$alkoxy groups, benzyl which is unsubstituted or is substituted on the phenyl ring with 1–4 C$_1$-C$_4$alkyl and/or C$_1$-C$_4$alkoxy groups, or is C$_3$-C$_8$alkenyl, or R$_9$ is a radical of the formula IV or V, X is unsubstituted or —OR$_{13}$-substituted C$_1$-C$_{12}$alkylene, C$_3$-C$_{18}$alkylene which is interrupted by O, or is C$_4$-C$_8$alkenylene or xylylene, R$_{10}$ is C$_1$-C$_{12}$alkyl, C$_3$-C$_{18}$alkyl which is interrupted by O, or is C$_3$-C$_8$alkenyl, cyclopentyl, cyclohexyl or phenyl, or R$_9$ and R$_{10}$ in the formula IIIb are together —CH$_2$CH$_2$—, R$_{11}$ is hydrogen, C$_1$-C$_{12}$alkyl, C$_3$-C$_{18}$alkyl which is interrupted by O, or is C$_3$-C$_8$alkenyl, cyclopentyl, cyclohexyl, phenyl or —OR$_9$, and R$_{13}$ is C$_1$-C$_4$alkyl, for the curing of ethylenically unsaturated compounds with daylight or daylight-equivalent light sources, and to a method of curing ethylenically unsaturated polymerizable compounds, which comprises adding to these compounds at least one photoinitiator of the formula I as defined above and carrying out irradiation with daylight or daylight-equivalent light sources.

The invention likewise relates to the use of compounds of the formula I for the curing of shaped articles made from composite compositions, and to a process of curing shaped articles made from composite compositions using the above-defined compounds of the formula I.

The invention also relates to the use of the composition according to the invention for the production of coating substances, in particular white paints for wood coatings and metal coatings, or clearcoats, for the production of coating materials pigmented with coloured pigments, for the production of clear or pigmented aqueous dispersions, for the production of powder coatings, for the production of printing inks, for the production of three-dimensional articles by bulk curing or stereolithography, for the production of dental filling compositions, for the production of composite materials, for the production of printing plates, for the production of masks for screen printing, for the production of photoresists for printed electronic circuits, for the production of adhesives, as a coating for optical fibres or as a coating or encapsulation of electronic components.

The invention additionally relates to a process for the photopolymerization of compounds containing ethylenically unsaturated double bonds, which comprises irradiating a composition as described above with light in the range from 200 to 600 nm.

In accordance with the invention this process is also used for the production of coating substances, especially white paints for wood coatings and metal coatings, or clear coating materials, for the production of powder coatings, for the production of coating materials for daylight-curable constructional coatings and road markings, for the production of composite materials, for the production of printing plates, for the production of masks for screen printing, for the production of photoresists for printed electronic circuits, for the production of adhesives, for the production of coatings for optical fibres, for the production of coatings or encapsulations of electronic components, and in the method of bulk curing or stereolithography.

The invention likewise relates to a coated substrate which is coated on at least one surface with a cured composition as described above, and to a process for the photographic production of relief images in which a coated substrate is subjected to imagewise exposure and then the unexposed areas are removed with a solvent.

The compounds according to the invention exhibit good stability to hydrolysis. A further advantage is that they can be dissolved very readily in the mixtures to be polymerized, and are of only very low volatility. The yellowing values of the compositions cured using the compounds according to the invention are low, and surfaces having good gloss values are obtained. The compounds according to the invention are also highly suitable for the curing of relatively thick pigmented layers. Using the compounds according to the invention is it possible, for example, to cure layers up to 300 μm. The maximum curable layer thicknesses are dependent on the concentration of TiO$_2$. For example, TiO$_2$ contents of up to 50% are possible.

The compounds according to the invention are not very yellow themselves, and are therefore particularly suitable for use as initiators. Moreover, when irradiated the compounds according to the invention fade with particular rapidity, which is a factor in favour of their use as initiators, especially in polymerizable compositions which must not show any yellow coloration.

The examples which follow illustrate the invention in more detail. As in the remainder of the description and the patent claims, parts and percentages are by weight unless stated otherwise.

Where in the designations of alkyl radicals having more than 3 carbon atoms no specific isomers are indicated, these radicals are in each the n-isomers.

I) Preparation of the starting materials a) Bromination of aromatic compounds

EXAMPLE 1a 80 g of 1,3-dibutoxybenzene (0.36 mol) are dissolved at room temperature in 100 ml of carbon tetrachloride. 64.25 g of N-bromosuccinimide (0.36 mol) are introduced in portions over 30 minutes such that the temperature can be maintained between 20° C. and 30° C. When the addition is complete, the mixture is stirred at room temperature for 1 hour. The reaction mixture is filtered over kieselguhr and the solvent is removed completely by concentration. The crude product (110 g) is fractionated on a 10 cm Vigreux column at 10$^{-1}$ mbar. In this way, 65 g of 1-bromo-2,4-dibutoxybenzene with a boiling point of 112° C. at 10$^{-1}$ mbar are obtained as a yellowish oil in 60% yield.

EXAMPLES 2a–18a

The compounds of Examples 2a–18a are prepared by the same method as described in Example 1a.

The compounds and their boiling points are listed in Table 1.

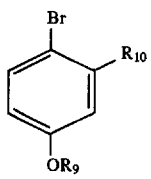

TABLE 1

| Ex. | R₉ | R₁₀ | b.p. or m.p. |
|---|---|---|---|
| 2a | —$C_2H_5$ | —H | 36° C./10⁻¹ mbar |
| 3a | —$C_3H_7$ | —H | 43° C./10⁻¹ mbar |
| 4a | —$C_4H_9$ | —H | 52° C./10⁻¹ mbar |
| 5a | —CH(CH₃)C₂H₅ | —H | 65° C./10⁻¹ mbar |
| 6a | -Phenyl | —H | 92° C./10⁻¹ mbar |
| 7a | —CH₃ | —OCH₃ | 69° C./10⁻¹ mbar |
| 8a | —C₂H₅ | —OC₂H₅ | 86° C./10⁻¹ mbar |
| 9a | —C₃H₇ | —OC₃H₇ | 96° C./10⁻¹ mbar |
| 10a | —CH(CH₃)₂ | —OCH(CH₃)₂ | 72° C./10⁻¹ mbar |
| 11a | —CH₂CH(CH₃)₂ | —OCH₂CH(CH₃)₂ | 112° C./10⁻¹ mbar |
| 12a | —C₈H₁₇ | —OC₈H₁₇ | Oil |
| 13a | —CH₂CH₂OCH₃ | —OCH₂CH₂OCH₃ | 135° C./10⁻² mbar |
| 14a | —C₅H₁₁ | —OC₅H₁₁ | 139° C./10⁻¹ mbar |
| 15a | —C₆H₁₃ | —OC₆H₁₃ | 155° C./10⁻¹ mbar |
| 16a | —CH₂-Phenyl | —OCH₂-Phenyl | m.p. < 20° C. |
| 17a | —CH(CH₃)C₂H₅ | —OCH(CH₃)C₂H₅ | 105° C./0.04 mbar |
| 18a | —C₄H₉ | —CH₃ | 89° C./10⁻¹ mbar |

EXAMPLES 20a–25a

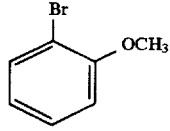
20a

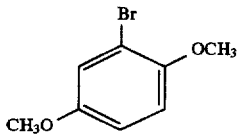
21a

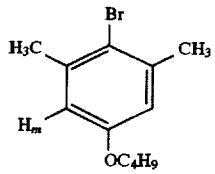
22a

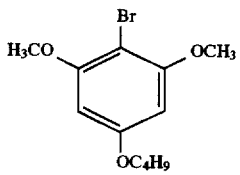
23a

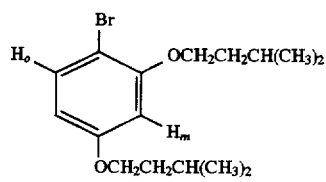
24a

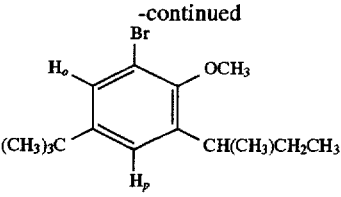
25a

The compounds are obtained in analogy to the method described in Example 1a. The boiling point of compound 20a is 223° C., that of compound 21a is 131° C./10 mmHg. Specific ¹H NMR shift values δ for the compound 22a are: OCH₂ (triplet) 3.90 ppm, $H_m$ 6.36 ppm. Compound 23a is commercially available (melting point 99° C.). Specific ¹H NMR shift values δ for the compound 24a are: Ho (doublet) 3.75 ppm, $H_m$ (fine doublet) 6.47 ppm. Specific ¹H NMR shift values δ for the compound 25a are: OCH₃ 3.80 ppm, $H_o$ 7.36 ppm, Hp 7.13 ppm.

b) Synthesis of the corresponding diethoxyphoslhine oxides

EXAMPLE 1b

Under a stream of nitrogen, 61 g of 1-bromo-2,4-dibutoxybenzene (0.20 mol) are heated together with 2.50 g of nickel(II) chloride (0.019 mol) to 160° C., and 46.3 g of triethyl phosphite (0.278 mol) are added dropwise over the course of 11/2 hours. The ethyl bromide formed in this process is distilled off from the reaction mixture continuously. After addition is complete, the mixture is stirred at 160° C. for 1 hour. The reaction mixture is then cooled to room temperature, 50 ml of diethyl ether are added, the mixture is filtered through kieselguhr and the solvent is removed completely by concentration. The crude product (82 g) is fractionated on a 10 cm Vigreux column at 10⁻¹ mbar. In this way, 42 g of diethyl (2,4-dibutoxyphenyl) phosphonate having a boiling point of 170° C. at 10⁻¹ mbar are obtained as a colourless oil in 60% yield.

EXAMPLES 2b–18b

The compounds of Examples 2b–18b are prepared by the same method as described in Example 1b. The compounds and their boiling points are compiled in Table 2.

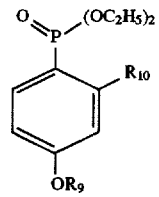

TABLE 2

| Ex. | R₉ | R₁₀ | b.p. or (m.p.) |
|---|---|---|---|
| 2b | —C₂H₅ | —H | 75° C./10⁻¹ mbar |
| 3b | —C₃H₇ | —H | 125° C./10⁻¹ mbar |
| 4b | —C₄H₉ | —H | 146° C./10⁻¹ mbar |
| 5b | —CH(CH₃)C₂H₅ | —H | 130° C./10⁻¹ mbar |
| 6b | -Phenyl | —H | 155° C./10⁻¹ mbar |
| 7b | —CH₃ | —OCH₃ | 155° C./10⁻¹ mbar |
| 8b | —C₂H₅ | —OC₂H₅ | 112° C./10⁻¹ mbar |
| 9b | —C₃H₇ | —OC₃H₇ | 153° C./10⁻¹ mbar |
| 10b | —CH(CH₃)₂ | —OCH(CH₃)₂ | 149° C./10⁻¹ mbar |
| 11b | —CH₂CH(CH₃)₂ | —OCH₂CH(CH₃)₂ | 155° C./10⁻¹ mbar |
| 12b | —C₈H₁₇ | —OC₈H₁₇ | Oil |

TABLE 2-continued

| Ex. | R₉ | R₁₀ | b.p. or (m.p.) |
|---|---|---|---|
| 13b | —CH₂CH₂OCH₃ | —OCH₂CH₂OCH₃ | 180° C./10⁻² mbar |
| 14b | —C₅H₁₁ | —OC₅H₁₁ | 179° C. |
| 15b | —C₆H₁₃ | —OC₆H₁₃ | 189° C. |
| 16b | —CH₂-Phenyl | —OCH₂-Phenyl | 86° C. (m.p.) |
| 17b | —CH(CH₃)C₂H₅ | —OCH(CH₃)C₂H₅ | 160° C./10⁻² mbar |
| 18b | —C₄H₉ | —CH₃ | 160° C. |

EXAMPLES 20b–25b

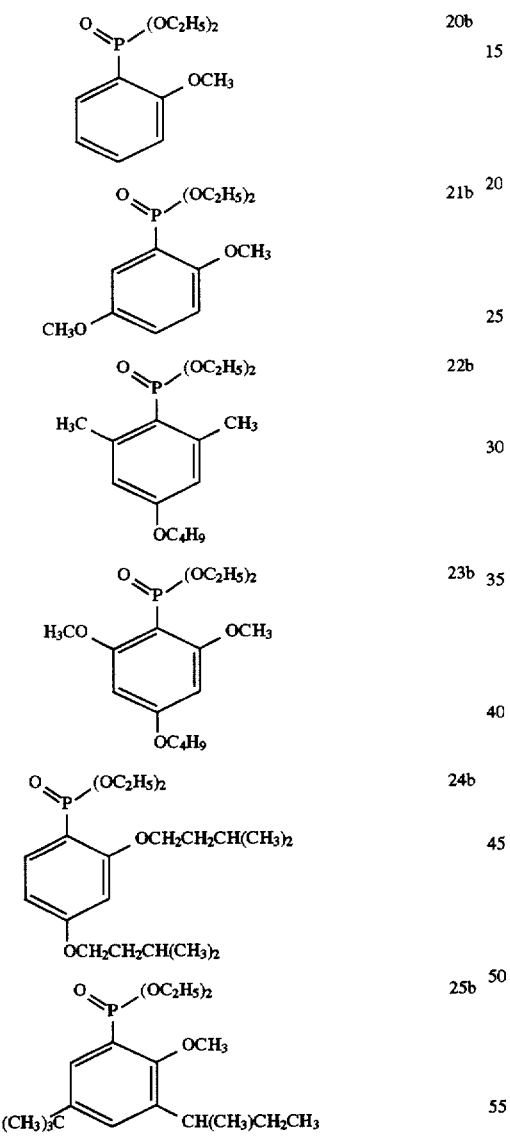

The compounds are obtained in analogy to the method described in Example 1b. The boiling points of the compounds are: 20b=138° C./10⁻¹ mbar, 21b=155° C./10⁻¹ mbar, 22b=100° C./10⁻¹ mbar, 23b=160° C./10⁻¹ mbar, 24b=180° C./10⁻¹ mbar, 25b=130° C./10⁻¹ mbar. The melting point of compound 23a is 60° C.

c) Hydrogenation of the phosphine oxides from b)

EXAMPLE 1c

Under a nitrogen atmosphere and with exclusion of moisture, 8.23 g of lithium aluminium hydride (0.217 mol) are suspended in 180 ml of diethyl ether, and at −10° C. 25.80 g of diethyl (2,4-dibutoxyphenyl)phosphonate (0.072 mol) are added dropwise over the course of 1½ hours. The reaction mixture is then stirred overnight at room temperature. At a temperature of between 0° and 5° C., hydrolysis is carried out with 8.0 g of water and then with 8.0 g of 15% strength NaOH and 24 g of water, carefully and with vigorous stirring, to produce a bulky precipitate. This precipitate is filtered off under argon over kieselguhr and washed with 50 ml of ether, and then the solvent is removed completely by concentration. In this way, 18.3 g of 2,4-dibutoxyphenylphosphine are obtained as a brownish oil in 92% yield.

EXAMPLES 2c–18c AND 20c–25c

The compounds are prepared by the same method as described in Example 1c. They are obtained as oils and used subsequently without further purification or characterization.

The compounds are depicted in Table 3

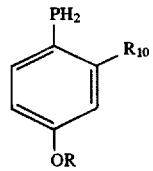

TABLE 3

| Ex. | R₉ | R₁₀ |
|---|---|---|
| 2c | —C₂H₅ | —H |
| 3c | —C₃H₇ | —H |
| 4c | —C₄H₉ | —H |
| 5c | —CH(CH₃)C₂H₅ | —H |
| 6c | -Phenyl | —H |
| 7c | —CH₃ | —OCH₃ |
| 8c | —C₂H₅ | —OC₂H₅ |
| 9c | —C₃H₇ | —OC₃H₇ |
| 10c | —CH(CH₃)₂ | —OCH(CH₃)₂ |
| 11c | —CH₂CH(CH₃)₂ | —OCH₂CH(CH₃)₂ |
| 12c | —C₈H₁₇ | —OC₈H₁₇ |
| 13c | —CH₂CH₂OCH₃ | —OCH₂CH₂OCH₃ |
| 14c | —C₅H₁₁ | —OC₅H₁₁ |
| 15c | —C₆H₁₃ | —OC₆H₁₃ |
| 16c | —CH₂-Phenyl | —OCH₂-Phenyl |
| 17c | —CH(CH₃)C₂H₅ | —OCH(CH₃)C₂H₅ |
| 18c | —C₄H₉ | —CH₃ |

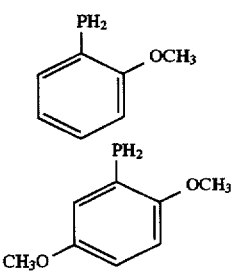

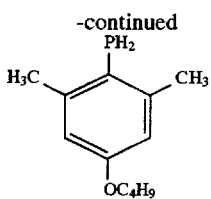

22c

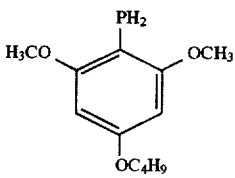

23c

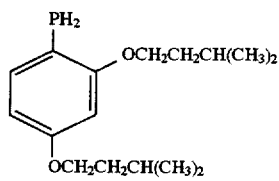

24c

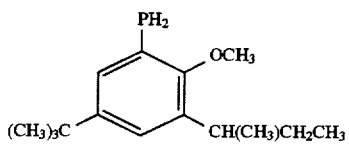

25c

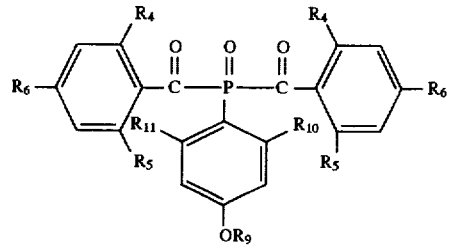

II) Preparation of the compounds according to the invention

EXAMPLE 1

Under a nitrogen atmosphere and with exclusion of moisture, 16.20 g of diisopropylamine (0.16 mol) are dissolved in 50 ml of tetrahydrofuran, and 100 ml of butyllithium (1.6M in hexane (0.16 mol)) are added dropwise with stirring at between −10° C. and 10° C. over the course of 20 minutes. The freshly prepared lithium diisopropylamide (LDA) is added dropwise over the course of 90 minutes at between −40° C. and −30° C. to a solution of 18.30 g of 2,4-dibutoxyphenylphosphine (0.072 mol) and 29.2 g of 2,4,6-trimethylbenzoyl chloride (0.16 mol) in 150 ml of tetrahydrofuran. When the addition is complete, stirring is continued at −30° C. for 2 hours and at room temperature overnight. At the same temperature, 50 ml of water are added dropwise to the solution, which is now yellow, the phases are separated, the organic phase is dried over $MgSO_4$ and filtered, and the solvent is removed completely by concentration. 40 g of yellowish oil in the P(III) state are obtained. This product is dissolved in 100 ml of toluene, and is oxidized at between 50° C. and 60° C. with 8.20 g of 30% strength hydrogen peroxide dropwise over the course of 1 hour. When the reaction has ended the mixture is cooled to room temperature, the phases are separated, and washing is carried out with 30 ml of water, 30 ml of 10% strength sodium hydrogen carbonate solution and then with water until a neutral pH is obtained. Drying over $MgSO_4$ and complete removal of the solvent by concentration give 38 g of yellow oil in the P(V) state.

Following chromatographic purification and recrystallization from petroleum ether, 20 g of bis(2,4,6-trimethylbenzoyl)-(2,4-dibutoxyphenyl)phosphine oxide are obtained in 50% yield as a yellowish solid having a melting point of 118° C. to 119° C.

| Elemental analysis: | C | H |
|---|---|---|
| calculated | 72.53% | 7.70% |
| found | 72.65% | 8.07% |

EXAMPLES 2-19

The compounds of Examples 2-19 are prepared in analogy to the method described in Example 1 using the corresponding starting materials of the formulae 2c to 19c. In order to prepare the compound of Example 19, 2,6-dimethoxybenzoyl chloride is used instead of 2,4,6-trimethylbenzoyl chloride. The compounds and their physical data are compiled in Table 4 below.

TABLE 4

| Ex. | $R_4 = R_5$ | $R_6$ | $R_9$ | $R_{10}$ | $R_{11}$ | m.p. [°C.] | calculated C % | H % | found C % | H % |
|---|---|---|---|---|---|---|---|---|---|---|
| 2 | $CH_3$ | $CH_3$ | $C_2H_5$ | H | H | 120 | 72.71 | 6.76 | 72.75 | 7.20 |
| 3 | $CH_3$ | $CH_3$ | $C_3H_7$ | H | H | 101 | 73.09 | 6.98 | 72.95 | 6.95 |
| 4 | $CH_3$ | $CH_3$ | $C_4H_9$ | H | H | 102 | 73.45 | 7.19 | 73.26 | 7.20 |
| 5 | $CH_3$ | $CH_3$ | $CH(CH_3)C_2H_5$ | H | H | 115 | 73.45 | 7.19 | 73.42 | 7.18 |
| 6 | $CH_3$ | $CH_3$ | Phenyl | H | H | 98 | 75.28 | 6.12 | 75.23 | 6.14 |
| 7 | $CH_3$ | $CH_3$ | $CH_3$ | $OCH_3$ | H | 177 | 70.28 | 6.53 | 70.00 | 6.62 |
| 8 | $CH_3$ | $CH_3$ | $C_2H_5$ | $OC_2H_5$ | H | 182 | 71.13 | 6.96 | 71.26 | 7.27 |
| 9 | $CH_3$ | $CH_3$ | $C_3H_7$ | $OC_3H_7$ | H | 159 | 71.89 | 7.35 | 71.99 | 7.34 |
| 10 | $CH_3$ | $CH_3$ | $CH(CH_3)_2$ | $OCH(CH_3)2$ | H | 170 | 71.89 | 7.35 | 71.82 | 7.39 |
| 11 | $CH_3$ | $CH_3$ | $CH_2CH(CH_3)_2$ | $OCH_2CH(CH_3)_2$ | H | 146 | 72.58 | 7.70 | 72.42 | 7.82 |
| 12 | $CH_3$ | $CH_3$ | $C_8H_{17}$ | $OC_8H_{17}$ | H | 75 | 74.75 | 8.81 | 74.68 | 8.87 |
| 13 | $CH_3$ | $CH_3$ | $CH_2CH_2OCH_3$ | $OCH_2CH_2OCH_3$ | H | 130 | 67.83 | 6.94 | 67.66 | 7.04 |

TABLE 4-continued

| Ex. | $R_4 = R_5$ | $R_6$ | $R_9$ | $R_{10}$ | $R_{11}$ | m.p. [°C.] | calculated C % | calculated H % | found C % | found H % |
|---|---|---|---|---|---|---|---|---|---|---|
| 14 | $CH_3$ | $CH_3$ | $C_5H_{11}$ | $OC_5H_{11}$ | H | 91 | 73.20 | 8.02 | 73.10 | 8.15 |
| 15 | $CH_3$ | $CH_3$ | $C_6H_{13}$ | $OC_6H_{13}$ | H | 102 | 73.76 | 8.31 | 73.62 | 8.42 |
| 16 | $CH_3$ | $CH_3$ | $CH_2$Phenyl | $OCH_2$Phenyl | H | 141 | 76.16 | 6.24 | 75.98 | 6.28 |
| 17 | $CH_3$ | $CH_3$ | $CH(CH_3)C_2H_5$ | $OCH(CH_3)C_2H_5$ | H | 118 | 72.58 | 7.70 | 72.51 | 7.78 |
| 18 | $CH_3$ | $CH_3$ | $C_4H_9$ | $CH_3$ | H | 81 | 73.79 | 7.39 | 73.77 | 7.38 |
| 19 | $OCH_3$ | H | $C_4H_9$ | $OC_4H_9$ | H | 129 | 64.21 | 6.57 | 64.12 | 6.65 |
| 20 | $OCH_3$ | H | $C_4H_9$ | $CH_3$ | H | 128 | 64.44 | 6.15 | 64.39 | 6.29 |
| 21 | $OCH_3$ | H | $C_8H_{17}$ | $OC_6H_{17}$ | H | 82 | 67.59 | 7.80 | 67.13 | 7.79 |
| 22 | $CH_3$ | $CH_3$ | $C_4H_9$ | $CH_3$ | $CH_3$ | 118 | 74.11 | 7.58 | 74.14 | 7.70 |
| 23 | $CH_3$ | $CH_3$ | $CH_3$ | $OCH_3$ | $OCH_3$ | 181 | 68.49 | 6.54 | 68.63 | 6.60 |
| 24 | $CH_3$ | $CH_3$ | $(CH_2)_2CH(CH_3)_2$ | $O(CH_2)_2CH(CH_3)_2$ | H | 102 | 73.20 | 8.02 | 73.22 | 8.05 |

EXAMPLE 25

Preparation of bis(2,4,6-trimethylbenzoyl)-2-methoxyphenylphosphine oxide The title compound is obtained by the method described in Example 1 using the compound of Example 20c as starting material, and has a melting point of 1680C.

Elemental analysis: calc.: C: 72.31% found.: C: 72.33% H: 6.52% H: 6.71%

EXAMPLE 26

Preparation of bis(2,4,6-trimethylbenzoyl)-2,5-dimethoxyphenylphosphine oxide

The title compound is obtained by the method described in Example 1 using the compound of Example 21c as starting material, and has a melting point of 161° C.

Elemental analysis: calc.: C: 70.28% found.: C: 70.41% H: 6.53% H: 6.50%

EXAMPLE 27

Preparation of bis[2,4,6-trimethylbenzoyl]-(3-i-butyl-5-t-butyl-2-methoxyphenyl]phosphine oxide The title compound is obtained by the method described in Example 1 using the compound of Example 25c as starting material, and has a melting point <20° C.

Elemental analysis: calc.: C: 74.84% found.: C: 74.79% H: 8.25% H: 8.25%

III) Use Examples

EXAMPLE 28

Photoinitiator according to the invention in a clearcoat A UV-curable clearcoat is prepared by mixing
99.5 parts of ®Roskydal 502 (=66% unsaturated polyester resin and 34% styrene; from Bayer) and
0.5 part of Byk 300 (levelling assistant; from Byk-Mallinckrodt)
2 parts of a photoinitiator mixture comprising 95% of 1-benzoyl-1-hydroxy-1-methylethane and 5% of the photoinitiator of Example 1 are incorporated into this coating formulation. The coating material is applied to a chipboard panel using a 200 82 m slotted doctor knife and then cured. Curing is carried out by conveying the sample, on a conveyor belt which moves at a speed of 3 n/min. beneath two 80 W/cm medium-pressure mercury lamps (Aetek, USA). The pendulum hardness (in accordance with König, DIN 53157) of the smearproof coating is determined. The results are compiled in Table 5.

TABLE 5

| Compound of Ex. | Pendulum hardness [s] |
|---|---|
| 1 | 94 |
| 2 | 106 |
| 3 | 104 |
| 4 | 105 |
| 5 | 104 |
| 6 | 94 |
| 7 | 104 |
| 8 | 106 |
| 9 | 109 |
| 10 | 108 |
| 11 | 104 |
| 12 | 401 |
| 25 | 104 |
| 26 | 102 |

EXAMPLE 29

Photoinitiator according to the invention in a white paint
A UV-curable white paint is prepared by mixing 67.5 parts of ®Ebecryl 830 (polyester acrylate from UCB, Belgium)
5.0 parts of 1,6-hexanediol diacrylate
2.5 parts of trimethylolpropane triacrylate
25.0 parts of R-TC2 (rutile titanium dioxide; from Tioxide) and
2.0 parts of the compound according to the invention.

The paint is applied to a chipboard panel using a 150 µm slotted doctor knife and then cured. Curing is carried Out by conveying the sample, on a conveyor belt which moves at a speed of 3 m/min. beneath a 120 W/cm fusion D lamp and a 80 W/cm medium-pressure mercury lamp (Hanovia, USA). The panel is subsequently after-exposed using fluorescent lamps of the Philips TL40W/03 type for 15 minutes. The König pendulum hardness (PH) (DIN 53157) and the Yellowness Index (YI) in accordance with ASTM D 1925-70 are determined. The higher the pendulum hardness, the more reactive the initiator. The lower the YI value, the lower the yellowing. The results are reproduced in Table 6.

TABLE 6

| Compound of Ex. | PH [s] | YI |
| --- | --- | --- |
| 1 | 131 | 0.9 |
| 2 | 157 | 2.0 |
| 3 | 160 | 1.9 |
| 4 | 168 | 1.9 |
| 5 | 136 | 1.6 |
| 6 | 136 | 1.2 |
| 7 | 143 | 1.6 |
| 10 | 138 | 1.3 |
| 11 | 142 | 1.5 |
| 12 | 144 | 1.0 |
| 26 | 154 | 1.2 |

EXAMPLE 30

Photoinitiator according to the invention in a white paint
A UV-curable white paint is prepared by mixing
76.5 parts of ®Ebecryl 830 (polyester acrylate from UCB, Belgium)
5.7 parts of 1,6-hexanediol diacrylate
2.8 parts of trimethylolpropane triacrylate
15.0 parts of R-TC2 (rutile titanium dioxide; from Tioxide) and
1.6 parts of a photoinitiator mixture comprising 38% by weight of the
compound according to the invention to be tested and 62% by weight of 1-benzoyl-1-hydroxy-1-methylethane. The paint is applied to a chipboard panel using a 150 μm slotted doctor knife and then cured. Curing is carried out by conveying the sample twice on a conveyor belt which moves at a speed of 10 m/min, beneath a 120 W/cm fusion D lamp and a 80 W/cm medium-pressure mercury lamp (Hanovia, USA). The panel is subsequently after-exposed using fluorescent lamps of the Philips TL40W/03 type for 15 minutes. The König pendulum hardness (PH) (DIN 53157) and the Yellowness Index (YI) in accordance with ASTM D 1925-70 are determined. The higher the pendulum hardness, the more reactive the initiator. The lower the YI value, the lower the yellowing. The results are reproduced in Table 7.

TABLE 7

| Compound of Ex. | PH [s] | YI |
| --- | --- | --- |
| 1 | 139 | −0.2 |
| 11 | 144 | −0.1 |

EXAMPLE 31

Curing of a white paint formulation with sunlight A white paint formulation is prepared from
67.5 parts of ®Ebecryl 830 (polyester acrylate from UCB, Belgium)
5.0 parts of 1,6-hexanediol diacrylate
2.5 parts of trimethylolpropane triacrylate
25.0 parts of R-TC2 (rutile titanium dioxide; from Tioxide) and
2.0 parts of the photoinitiator compound of Example 18.

The formulation is applied to coil-coated aluminium panels using a 100μ slotted doctor knife and exposed to direct sunlight (irradiation intensity=25 W/cm²). After 10 minutes the coating has cured right through and is tack-free on the surface.

EXAMPLE 32

The white paint formulation of Example 31 is applied to chipboard panels in coats 1 mm thick and curing is then carried out beneath two 80 W/cm medium-pressure mercury lamps (Aetek, USA) at a belt speed of 10 m/min. The upper, cured coat is then separated from the liquid substrate, washed with acetone and dried. The coat thickness of the resulting coating film is measured. The results are compiled in Table 8.

TABLE 8

| Compound from Ex. | Coat thickness [μm] |
| --- | --- |
| 11 | 142 |
| 12 | 143 |
| 13 | 145 |
| 14 | 140 |
| 15 | 140 |
| 17 | 143 |

EXAMPLE 33

Curing of a laminated composite composition A formulation is prepared from
98.0 parts of ®Roskydal 500A, unsaturated polyester/styrene (Bayer, Germany)
1.0 part of the photoinitiator of Example 14
1.0 part of benzoyl peroxide.

A lamina, comprising 6 layers of a glass fibre mat, and the above formulation are fly compressed. The weight ratio of glass fibre mat to formulation is 1:1. The assembly is then exposed for one minute under lamps of the TL40W/03 type (Philips), in the course of which the composition is partially cured. It is then heated in an oven at 170° C. for 30 minutes, in the course of which complete curing takes place to give a highly stable composite composition.

EXAMPLE 34

Preparation of a flexographic printing plate
a) 1.13 parts of ®Irganox 565 (antioxidant; Ciba-Geigy, Switzerland), 0.03 part of ®Ceres Black (pigment, Sudan Black No. 86015; Fluka, Switzerland)and 0.3% or 0.4% of the photoinitiator to be tested are dissolved in 41.54 parts of 1,6-hexanediol diacrylate (HDDA) with stirring for 30 minutes at not more than 50 ° C. 332.30 parts of ®Cariflex TR 1107 (block polymer of polyisoprene and polystyrene; Shell Chemie, Netherlands) with 2 g of excess are melted at 140° C. on a calender for 10 min to form a sheet. At 110 ° C., the dropwise addition of the HDDA solution made up beforehand is commenced. This dropwise addition lasts for about 15 min. Thereafter, the entire formulation is homogenized on the calender at 100° C. for a further 15 min. After removal from the calender, the coarse sheet is placed between two Teflon sheets and cooled at a pressure of 100 kp/cm² in a water-cooled press. 70 g of the sheet are enclosed in a 2 mm thick pressing frame between two 76 μm polyester films and pressed to give 2 mm thick plates, by first heating the "sandwich" for one minute without applying pressure between the faces of a second press, preheated to 90° C., and then pressing it for 10 min at a pressure of 200 kp/cm². The "sandwich" is then cooled in the first water-cooled press to 15° C., for 10 min at a pressing pressure of 200 kp/cm², and then cut out of the press frame.

b) Then, in order to determine the optimum exposure time for base formation of the plate covered on both sides with polyester film, a strip measuring 4×24 cm is cut out. This strip is exposed stepwise in a BASF Nyloprint exposure unit fitted with 20 W Nyloprint 2051 tubes by moving a mask between 9 exposure steps each lasting 20 s. This produces on the strip a curing pattern comprising ten sections, corresponding to the exposure times, 0, 20, 40, 60, 80, 100, 120, 140, 160 and 180 s. The plate is rotated and a 1.5 cm broad central strip is covered in the lengthwise direction. The entire structure is covered with a thin UV-transparent film, sucked against the exposure stage by means of a vacuum, and exposed for 6 minutes. The exposed plate is developed by washing out the insufficiently crosslinked areas in a BASF Nyloprint circular washer at 20° C. using a washing solution comprising a 4:1 mixture of tetrachloroethylene and n-butanol. The plate is dried for one hour at 80° C. in a convection oven, left for 5 minutes, dipped in a 0.4% strength bromine solution for fixing, and dipped for 10 s in an aqueous solution of 1.15% sodium thiosulfate/sodium carbonate for neutralization. The plate is then rinsed with demineralized water for 30 s. The central strip of the plate treated in this way is evaluated. The exposure time which results in the formation of a 1,400 µm base (=reverse side exposure time) is determined.

c) A piece of a plate sandwich produced as under a) is exposed over its entire surface for the exposure time determined under b) in order to form a plate base. The plate is then rotated, the polyester film is removed and a test negative having 4 fields is applied. Exposure of the 4 test fields of the test negative is carried out in steps using a movable mask. The first field is exposed for 6 min, and the exposure time of fields 2–4 is increased by one minute from field to field. The plate is developed and fixed as described above. The plate is then exposed over its entire surface on both sides for a further 6 min. The exposure time for achieving a shade value of 2% and 3% (=front side exposure time) is determined.

The perforation depth of the finished printing plate is measured using the microscope, and the relief height using a layer thickness measuring device. The results are revealed in Table 9.

TABLE 9

| Compound of Ex. | Concentration [%] | Reverse side exposure time [s] | Front side exposure time to shade value | | Perforation depth [m] | Relief height [m] |
|---|---|---|---|---|---|---|
| | | | 2% | 3% | | |
| 11 | 0.3 | 80 | 8 | 6 | 10 | 480–550 |
| 11 | 0.4 | 80 | 9 | 6 | 10 | 600–650 |
| 14 | 0.3 | 80 | 8 | 6 | — | 450–600 |
| 14 | 0.4 | 85 | 7 | 6 | 20 | 450–550 |
| 15 | 0.3 | 70 | 8 | 6 | 10 | 400–420 |
| 15 | 0.4 | 65 | 7 | 6 | 12 | 500–540 |
| 17 | 0.3 | 70 | 6 | 6 | 20 | 380–400 |
| 17 | 0.4 | 75 | >9 | 7 | 10 | 600–650 |

EXAMPLE 35

Reactivity test in a clearcoat (etch resist) A photocurable composition is prepared by mixing the following components:

50.0 g of urethane acrylate ®Actilan AJ20, Société National des Poudres et Explosifs
10.0 g of dipentaerythritol monohydroxy-pentaacrylate, ®SR 399, Sartomer Co.
15.0 g of tripropylene glycol diacrylate, Sartomer Co.
15.0 g of N-vinylpyrrolidone, Fluka
10.0 g of trimethylolpropane triacrylate, Degussa
0.3 g of levelling assistant ®Byk 300, Byk-Mallinckrodt.

Portions of this composition are mixed with 0.4% or 1%, based on the overall quantity, of the photoinitiator according to the invention by stirring at 60° C. for one hour.

All operations are carried out under red light. The initiator-treated samples are applied to 300 µm aluminium foil using a 100 µm doctor knife. The thickness of the dry film is 60–70 µm. A 76 µm thick polyester film is applied to this film, and on top of the polyester film is placed a standardized test negative with 21 steps of different optical density (Stauffer wedge). The sample is covered with a second UV-transparent film and pressed onto a metal plate by means of vacuum. Exposure takes place in a first test series for 5 seconds, in a second series for 10 seconds and then in a third series for 20 seconds, using an iron-doped Sylvania M061/5 kW lamp at a distance of 30 cm. After exposure, the films and the mask are removed and the exposed film is developed in ethanol for 10 seconds in an ultrasound bath at 23° C. Drying is then carried out in a convection oven at 40° C. for 5 minutes. The sensitivity of the initiator system used is characterized by indicating the last wedge step which is imaged without tackiness. The higher the number of steps, the more sensitive the system tested. The results are compiled in Table 10.

TABLE 10

| Compound from Ex. | Concentration [%] | Number of imaged steps after exposure time of | | |
|---|---|---|---|---|
| | | 5 s | 10 s | 20 s |
| 15 | 0.4 | 10 | 13 | 15 |
| 15 | 1.0 | 12 | 14 | 17 |
| 14 | 1.0 | 12 | 14 | 17 |
| 14 | 0.4 | 10 | 12 | 15 |

EXAMPLE 36

Photocuring of an acrylate mixture

A photocurable composition is prepared by mixing the following components:

| | Solids content |
|---|---|
| 150.30 g of ® Scripset 540 (30% solution of polystyrene-maleic anhydride copolymer in acetone); Monsanto | 45.1 g |
| 48.30 g of trimethylolpropane triacrylate | 48.3 g |
| 6.60 g of polyethylene glycol diacrylate | 6.6 g |
| | 100.0 g |

Portions of this composition are mixed in each case with 0.4% and 1%, based on the solids content, of photoinitiator. All operations are carried out under red light or yellow light. The initiator-treated samples are applied in a thickness of 150 µm to 200 µm aluminium foil (10×15 cm). The solvent is removed by heating at 60° C. in a convection oven for 15 minutes. A 76 µm thick polyester film is placed on the liquid layer, and a standardized test negative with 21 steps of different optical density (Stauffer wedge) is placed on this film. Over this assembly, a second polyester film is applied, and the resulting laminate is fixed on a metal plate. The sample is then exposed with a M061/5 kW lamp at a distance of 30 cm for 10 seconds in a first test series, 20 seconds in a second series and 40 seconds in a third series. After exposure, the films and the mask are removed, and the exposed layer is developed with a 0.85% aqueous solution of sodium carbonate for 120 seconds in an ultrasound bath, and then dried at 60° C. in a convection oven for 15 minutes. The sensitivity of the initiator system used is characterized by indicating the last wedge step which is imaged without tack. The higher the number of steps, the more sensitive the system. In this context, an increase by two steps signifies approximately a doubling in the curing rate. The results are depicted in Table 11.

TABLE 11

| Compound from Ex. | Concen- tration [%] | Number of imaged steps after exposure time of | | |
|---|---|---|---|---|
| | | 10 s | 20 s | 40 s |
| 15 | 0.4 | 8 | 10 | 12 |
| 15 | 1.0 | 10 | 12 | 14 |
| 14 | 0.4 | 8 | 10 | 12 |
| 14 | 1.0 | 10 | 12 | 15 |

EXAMPLE 37

Photocuring of a monomer-polymer mixture (reactivity test in a solder resist)

A photocurable composition is prepared by mixing the following components:

```
37.64 g of ® Sartomer SR 444, pentaerythritol triacrylate
        (Sartomer Company, Westchester)
10.76 g of ® Cymel 301, hexamethoxymethylmelamine (Cyanamid)
47.30 g of ® Carboset 525, thermoplastic polyacrylate
        containing carboxyl groups (B. F. Goodrich)
 4.30 g of polyvinylpyrrolidone PVP (GAF)

100.00 g of this composition are mixed with
319.00 g of methylene chloride and
 30.00 g of methanol.
```

Portions of this composition are mixed in each case with 0.4% and 1%, based on the solids content, of the photoinitiator to be tested. All operations are carried out under red light. The initiator-treated samples are applied in at a dry film thickness of 35 μm to a 200 μm aluminium foil (10×15 cm). The solvent is removed by heating at 60° C. in a convection oven for 15 minutes. A 76 μm thick polyester film is placed on the liquid layer, and a standardized test negative with 21 steps of different optical density (Stauffer wedge) is applied to this film. The sample is covered with a second UV-transparent film and pressed by means of vacuum onto a metal plate. The sample is then exposed with a MO61/5 kW lamp at a distance of 30 cm, for 10 seconds in a first test series, 20 seconds in a second test series and 40 seconds in a third test series. After exposure, the films and the mask are removed, the coated layer is developed with a 0.85% aqueous solution of sodium carbonate in an ultrasound bath for 240 seconds and then dried at 60° C. in a convection oven for 15 min. The sensitivity of the initiator system used is characterized by indicating the last wedge step which is imaged without tack. The higher the number of steps, the more sensitive the system. In this context, an increase by two steps signifies approximately a doubling in the curing rate. The results are indicated in Table 12.

TABLE 12

| Compound from Ex. | Concen- tration [%] | Number of imaged steps after exposure time of | | |
|---|---|---|---|---|
| | | 10 s | 20 s | 40 s |
| 15 | 0.4 | 7 | 9 | 11 |
| 15 | 1.0 | 9 | 11 | 13 |
| 14 | 0.4 | 8 | 10 | 12 |
| 14 | 1.0 | 10 | 12 | 15 |

What is claimed is:

1. A photopolymerizable composition comprising (a) at least one ethylenically unsaturated photopolymerizable compound; and (b) as photoinitiator, at least one compound of the formula I $$R_1-\underset{\underset{R_3}{|}}{\overset{\overset{O}{\|}}{C}}-\overset{\overset{O}{\|}}{P}-\overset{\overset{O}{\|}}{C}-R_2, \quad (I)$$

in which $R_1$ and $R_2$ are identical or different and are a radical of the formula II

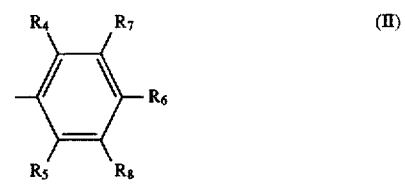

(II)

in which $R_4$ and $R_5$ independently of one another are $C_1$–$C_{12}$alkyl or $C_1$–$C_{12}$alkoxy, and $R_6$, $R_7$, $R_8$ independently of one another are hydrogen, $C_1$–$C_{12}$alkyl, $C_1$–$C_{12}$alkoxy or halogen, $R_3$ is a radical of the formula III

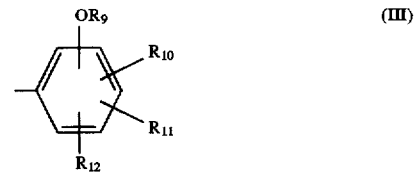

(III)

in which $R_9$ is $C_1$–$C_{20}$alkyl, $C_2$–$C_{20}$ alkyl which is interrupted by O, $C_2$–$C_{12}$alkenoxy-substituted $C_1$–$C_4$alkyl, halogen-substituted $C_1$–$C_{20}$alkyl, $C_5$–$C_6$cycloalkyl, phenyl which is unsubstituted or is substituted with 1–4 $C_1$–$C_4$alkyl and/or $C_1$–$C_4$alkoxy groups, naphthyl which is unsubstituted or is substituted with 1–4 $C_1$–$C_4$alkyl and/or $C_1$–$C_4$alkoxy groups, phenyl-$C_1$–$C_5$alkyl which is unsubstituted or is substituted on the phenyl ring with 1–4 $C_1$–$C_4$alkyl and/or $C_1$–$C_4$alkoxy groups, or is $C_2$–$C_{12}$alkenyl, —$CF_3$ or

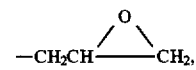

or $R_9$ is a radical of the formula IV or V

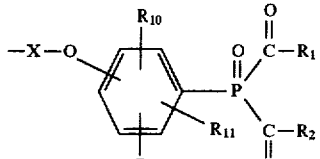

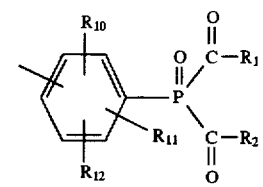

in which $R_1$ and $R_2$ are as defined above.

X is unsubstituted or $-OR_{13}$-substituted $C_1-C_{16}$alkylene, $C_2-C_{20}$alkylene which is interrupted by O, or is $C_4-C_{12}$alkenylene or xylylene, $R_{10}$ is hydrogen, $C_1-C_{20}$alkyl, $C_2-C_{18}$alkyl which is interrupted by O, or is $C_2-C_{12}$alkenyl, cyclopentyl, cyclohexyl, phenyl which is unsubstituted or is substituted with 1 or 2 $C_1-C_4$alkyl and/or $C_1-C_4$alkoxy groups, or is $C_1-C_4$alkoxy, $R_{11}$ is hydrogen, $C_1-C_{20}$alkyl, $C_2-C_{18}$alkyl which is interrupted by O, or is $C_2-C_{12}$alkenyl, cyclopentyl, cyclohexyl, phenyl which is unsubstituted or is substituted with 1 or 2 $C_1-C_4$alkyl and/or $C_1-C_4$alkoxy groups, or is $C_1-C_4$alkoxy, or is a radical of the formula VI

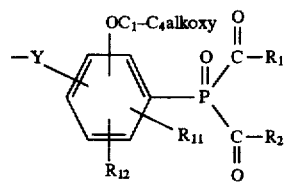

or $R_9$ and $R_{11}$ in the formula III together are $-CH_2CR_{14}R_{15}-$ or $-C(CH_3)_2CH=CH-$, or $R_{10}$ and $R_{11}$, together with the atoms to which they are attached, form a benzene ring which is unsubstituted or substituted with 1 or 2 $C_1-C_4$alkyl and/or $C_1-C_4$alkoxy groups, $R_{12}$ is hydrogen or $C_1-C_4$alkoxy, $R_{13}$ is $C_1-C_8$alkyl, $R_{14}$ and $R_{15}$ independently of one another are hydrogen, $C_1-C_8$alkyl, phenyl or $-CH_2O_{13}$, or $R_{14}$ and $R_{15}$, together with the carbon atom to which they attached, form a $C_5-C_6$cycloalkyl ring, Y is a single bond, $-CR_{16}R_{17}-$, $-NR_{18}-$, $-S-$, $-SO_2-$, $-(CH_2)_m$ or $-CH=CH-$, $R_{16}$ is hydrogen, methyl or ethyl, $R_{17}$ is hydrogen or $C_1-C_4$alkyl, $R_{18}$ is hydrogen, $C_1-C_{12}$alkyl or phenyl, and m is a number from 2-12, with the proviso that if the radical $-OR_9$ in the formula III is in the p-position of the phenyl ring and $R_9$ is methyl, at least one of the radicals $R_{10}$, $R_{11}$ and $R_{12}$ is not hydrogen.

2. A composition according to claim 1, comprising in addition to component (b) other photoinitiators and/or further additives.

3. A composition according to claim 2, in which the additional photoinitiators are compounds of the formula (VII)

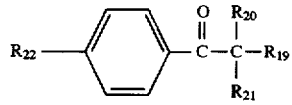

or (VII)

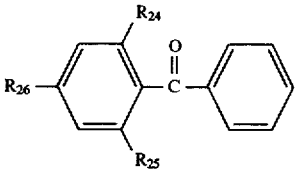

or mixtures of compounds of the formulae (VII) and (VIII), in which $R_{19}$ and $R_{20}$ independently of one another are hydrogen, $C_1-C_6$alkyl, phenyl, $C_1-C_{16}$alkoxy or $-O(CH_2CH_2O)_q-C_1-C_{16}$alkyl, in which q is a number from 1–20, or $R_{19}$ and $R_{20}$, together with the carbon atom to which they are attached, form a cyclohexyl ring, $R_{21}$ is hydroxyl, $C_1-C_{16}$alkoxy or $-O(CH_2CH_2O)_q-C_1-C_{16}$alkyl, where $R_{20}$, $R_{21}$ and $R_{22}$ are not all simultaneously $C_1-C_{16}$alkoxy or $-O(CH_2CH_2O)_q-C_1-C_{16}$alkyl, $R_{22}$ is hydrogen, $C_1-C_{18}$alkyl, $C_1-C_{18}$alkoxy, $-OCH_2CH_2-OR_{23}$, a group

or a group

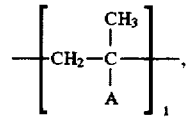

in which 1 has a value from 2 to 10 and A is the radical

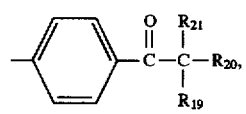

and $R_{23}$ is hydrogen,

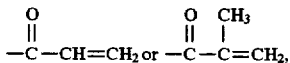

and $R_{24}$, $R_{25}$ and $R_{26}$ independently of one another are hydrogen or methyl.

4. A composition according to claim 1, comprising 0.05–15% by weight of component (b), based on the composition.

5. A coated substrate which is coated on at least one surface with a composition according to claim 1, wherein said composition is cured.

* * * * *